United States Patent
O'Connor et al.

(10) Patent No.: US 10,918,884 B2
(45) Date of Patent: Feb. 16, 2021

(54) FLUENCE MAP GENERATION METHODS FOR RADIOTHERAPY

(71) Applicant: RefleXion Medical, Inc., Hayward, CA (US)

(72) Inventors: Daniel O'Connor, Los Angeles, CA (US); Yevgen Voronenko, Sunnyvale, CA (US)

(73) Assignee: RefleXion Medical, Inc., Hayward, CA (US)

( * ) Notice: Subject to any disclaimer, the term of this patent is extended or adjusted under 35 U.S.C. 154(b) by 234 days.

(21) Appl. No.: 16/122,735

(22) Filed: Sep. 5, 2018

(65) Prior Publication Data
US 2019/0001152 A1 Jan. 3, 2019

Related U.S. Application Data

(63) Continuation of application No. PCT/US2017/021647, filed on Mar. 9, 2017.

(60) Provisional application No. 62/305,974, filed on Mar. 9, 2016.

(51) Int. Cl.
*A61N 5/10* (2006.01)
*G06K 9/32* (2006.01)

(52) U.S. Cl.
CPC .......... *A61N 5/1031* (2013.01); *A61N 5/10* (2013.01); *A61N 5/103* (2013.01); *A61N 5/1039* (2013.01); *A61N 5/1045* (2013.01); *G06K 9/3233* (2013.01); *A61N 2005/1034* (2013.01); *G06K 2209/05* (2013.01)

(58) Field of Classification Search
CPC ............ G06K 2209/05; G06K 9/3233; A61N 5/1031; A61N 5/1045; A61N 2005/1034; A61N 5/1039; A61N 5/10; A61N 5/103
See application file for complete search history.

(56) References Cited

U.S. PATENT DOCUMENTS

| | | | |
|---|---|---|---|
| 3,794,840 A | 2/1974 | Scott | |
| 3,906,233 A | 9/1975 | Vogel | |
| 3,987,281 A | 10/1976 | Hodes | |

(Continued)

FOREIGN PATENT DOCUMENTS

| | | |
|---|---|---|
| CN | 101739610 A | 6/2010 |
| CN | 201716569 U | 1/2011 |

(Continued)

OTHER PUBLICATIONS

Chen, X, et al. (2012). "Smoothing proximal gradient method for general structured sparse regression," The Annals of Applied Statistics 6:719-752. (Year: 2012).*

(Continued)

*Primary Examiner* — Christine H Matthews
*Assistant Examiner* — Joshua Daryl D Lannu
(74) *Attorney, Agent, or Firm* — Cooley LLP

(57) ABSTRACT

Described herein are methods for fluence map generation or fluence map optimization (FMO) for radiation therapy. One variation of a method for generating a fluence map comprises smoothing out nondifferentiable penalty functions and using an accelerated proximal gradient method (e.g., FISTA) to compute a fluence map that may be used by a radiotherapy system to apply a selected dose of radiation to one or more regions of interest (ROI) or volumes of interest (VOI).

35 Claims, 12 Drawing Sheets

(56) References Cited

U.S. PATENT DOCUMENTS

| | | | |
|---|---|---|---|
| 4,389,569 | A | 6/1983 | Hattori et al. |
| 4,503,331 | A | 3/1985 | Kovacs, Jr. et al. |
| 4,529,882 | A | 7/1985 | Lee |
| 4,563,582 | A | 1/1986 | Mullani |
| 4,575,868 | A | 3/1986 | Ueda et al. |
| 4,642,464 | A | 2/1987 | Mullani |
| 4,647,779 | A | 3/1987 | Wong |
| 4,677,299 | A | 6/1987 | Wong |
| 4,868,844 | A | 9/1989 | Nunan |
| 5,015,851 | A | 5/1991 | Singh et al. |
| 5,075,554 | A | 12/1991 | Yunker et al. |
| 5,206,512 | A | 4/1993 | Iwao |
| 5,207,223 | A | 5/1993 | Adler |
| 5,317,616 | A | 5/1994 | Swerdloff et al. |
| 5,329,567 | A | 7/1994 | Ikebe |
| 5,351,280 | A | 9/1994 | Swerdloff et al. |
| 5,390,225 | A | 2/1995 | Hawman |
| 5,394,452 | A | 2/1995 | Swerdloff et al. |
| 5,396,534 | A | 3/1995 | Thomas |
| 5,418,827 | A | 5/1995 | Deasy et al. |
| 5,442,675 | A | 8/1995 | Swerdloff et al. |
| 5,647,663 | A * | 7/1997 | Holmes ............... A61N 5/1031 600/407 |
| 5,751,781 | A | 5/1998 | Brown et al. |
| 5,813,985 | A | 9/1998 | Carroll |
| 5,818,902 | A | 10/1998 | Yu |
| 5,851,182 | A | 12/1998 | Sahadevan |
| 5,937,028 | A | 8/1999 | Tybinkowski et al. |
| 6,038,283 | A | 3/2000 | Carol et al. |
| 6,180,943 | B1 | 1/2001 | Lange |
| 6,184,530 | B1 | 2/2001 | Hines et al. |
| 6,188,748 | B1 | 2/2001 | Pastyr et al. |
| 6,239,438 | B1 | 5/2001 | Schubert |
| 6,260,005 | B1 | 7/2001 | Yang et al. |
| 6,281,505 | B1 | 8/2001 | Hines et al. |
| 6,385,288 | B1 | 5/2002 | Kanematsu |
| 6,393,096 | B1 | 5/2002 | Carol et al. |
| 6,438,202 | B1 | 8/2002 | Olivera et al. |
| 6,449,331 | B1 | 9/2002 | Nutt et al. |
| 6,449,340 | B1 | 9/2002 | Tybinkowski et al. |
| 6,455,856 | B1 | 9/2002 | Gagnon |
| 6,459,762 | B1 | 10/2002 | Wong et al. |
| 6,473,634 | B1 | 10/2002 | Barni |
| 6,504,899 | B2 | 1/2003 | Pugachev et al. |
| 6,552,693 | B1 | 4/2003 | Leisten |
| 6,560,311 | B1 | 5/2003 | Shepard et al. |
| 6,618,467 | B1 | 9/2003 | Ruchala et al. |
| 6,661,866 | B1 | 12/2003 | Limkeman et al. |
| 6,696,694 | B2 | 2/2004 | Pastyr et al. |
| 6,700,949 | B2 | 3/2004 | Susami et al. |
| 6,714,620 | B2 | 3/2004 | Caflisch et al. |
| 6,730,924 | B1 | 5/2004 | Pastyr et al. |
| 6,735,277 | B2 | 5/2004 | McNutt et al. |
| 6,794,653 | B2 | 9/2004 | Wainer et al. |
| 6,810,103 | B1 | 10/2004 | Tybinkowski et al. |
| 6,831,961 | B1 | 12/2004 | Tybinkowski et al. |
| 6,865,254 | B2 | 3/2005 | Näfstadius |
| 6,888,919 | B2 | 5/2005 | Graf |
| 6,914,959 | B2 | 7/2005 | Bailey et al. |
| 6,934,363 | B2 | 8/2005 | Seufert |
| 6,965,661 | B2 | 11/2005 | Kojima et al. |
| 6,976,784 | B2 | 12/2005 | Kojima et al. |
| 6,990,175 | B2 | 1/2006 | Nakashima et al. |
| 7,015,490 | B2 | 3/2006 | Wang et al. |
| 7,020,233 | B1 | 3/2006 | Tybinkowski et al. |
| 7,026,622 | B2 | 4/2006 | Kojima et al. |
| 7,110,808 | B2 | 9/2006 | Adair |
| 7,154,096 | B2 | 12/2006 | Amano |
| 7,167,542 | B2 | 1/2007 | Juschka et al. |
| 7,199,382 | B2 | 4/2007 | Rigney et al. |
| 7,227,925 | B1 | 6/2007 | Mansfield et al. |
| 7,242,750 | B2 | 7/2007 | Tsujita |
| 7,263,165 | B2 | 8/2007 | Ghelmansarai |
| 7,265,356 | B2 | 9/2007 | Pelizzari et al. |
| 7,266,175 | B1 | 9/2007 | Romesberg |
| 7,280,633 | B2 | 10/2007 | Cheng et al. |
| 7,291,840 | B2 | 11/2007 | Fritzler et al. |
| 7,297,958 | B2 | 11/2007 | Kojima et al. |
| 7,298,821 | B2 | 11/2007 | Ein-Gal |
| 7,310,410 | B2 | 12/2007 | Sohal et al. |
| 7,386,099 | B1 | 6/2008 | Kasper et al. |
| 7,397,901 | B1 | 7/2008 | Johnsen |
| 7,397,902 | B2 | 7/2008 | Seeber et al. |
| 7,453,983 | B2 | 11/2008 | Schildkraut et al. |
| 7,453,984 | B2 | 11/2008 | Chen et al. |
| 7,469,035 | B2 | 12/2008 | Keall et al. |
| 7,508,967 | B2 | 3/2009 | Harari et al. |
| 7,555,103 | B2 | 6/2009 | Johnsen |
| 7,558,378 | B2 | 7/2009 | Juschka et al. |
| 7,560,698 | B2 | 7/2009 | Rietzel |
| 7,564,951 | B2 | 7/2009 | Hasegawa et al. |
| 7,596,209 | B2 | 9/2009 | Perkins |
| 7,611,452 | B2 | 11/2009 | Allison et al. |
| 7,627,082 | B2 | 12/2009 | Kojima et al. |
| 7,639,853 | B2 | 12/2009 | Olivera et al. |
| 7,656,999 | B2 | 2/2010 | Hui et al. |
| 7,715,606 | B2 | 5/2010 | Jeung et al. |
| 7,742,575 | B2 | 6/2010 | Bourne |
| 7,755,055 | B2 | 7/2010 | Schilling |
| 7,755,057 | B2 | 7/2010 | Kim |
| 7,778,691 | B2 | 8/2010 | Zhang et al. |
| 7,792,252 | B2 | 9/2010 | Bohn |
| 7,795,590 | B2 | 9/2010 | Takahashi et al. |
| 7,801,270 | B2 | 9/2010 | Nord et al. |
| 7,835,494 | B2 | 11/2010 | Nord et al. |
| 7,839,972 | B2 | 11/2010 | Ruchala et al. |
| 7,949,095 | B2 | 5/2011 | Ning et al. |
| 7,957,507 | B2 | 6/2011 | Cadman |
| 7,965,819 | B2 | 6/2011 | Nagata |
| 7,983,380 | B2 | 7/2011 | Guertin et al. |
| 8,059,782 | B2 | 11/2011 | Brown |
| 8,063,376 | B2 | 11/2011 | Maniawski et al. |
| 8,073,103 | B2 | 12/2011 | Otto et al. |
| 8,077,936 | B2 | 12/2011 | Wang et al. |
| 8,085,899 | B2 | 12/2011 | Nord et al. |
| 8,116,427 | B2 | 2/2012 | Kojima et al. |
| 8,139,713 | B2 | 3/2012 | Janbakhsh |
| 8,139,714 | B1 | 3/2012 | Sahadevan |
| 8,144,962 | B2 | 3/2012 | Busch et al. |
| 8,148,695 | B2 | 4/2012 | Takahashi et al. |
| 8,149,991 | B2 | 4/2012 | More |
| 8,180,020 | B2 | 5/2012 | Kilby et al. |
| 8,232,535 | B2 | 7/2012 | Olivera et al. |
| 8,280,002 | B2 | 10/2012 | Bani-Hashemi et al. |
| 8,295,906 | B2 | 10/2012 | Saunders et al. |
| 8,304,738 | B2 | 11/2012 | Gagnon et al. |
| 8,335,296 | B2 | 12/2012 | Dehler et al. |
| 8,357,903 | B2 | 1/2013 | Wang et al. |
| 8,384,049 | B1 | 2/2013 | Broad |
| 8,406,844 | B2 | 3/2013 | Ruchala et al. |
| 8,442,287 | B2 | 5/2013 | Fordyce, II et al. |
| 8,461,539 | B2 | 6/2013 | Yamaya et al. |
| 8,467,497 | B2 | 6/2013 | Lu et al. |
| 8,483,803 | B2 | 7/2013 | Pertain et al. |
| 8,509,383 | B2 | 8/2013 | Lu et al. |
| 8,536,547 | B2 | 9/2013 | Maurer, Jr. et al. |
| 8,537,373 | B2 | 9/2013 | Humphrey |
| 8,581,196 | B2 | 11/2013 | Yamaya et al. |
| 8,588,367 | B2 | 11/2013 | Busch et al. |
| 8,617,422 | B2 | 12/2013 | Koschan et al. |
| 8,664,610 | B2 | 3/2014 | Chuang |
| 8,664,618 | B2 | 3/2014 | Yao |
| 8,712,012 | B2 | 4/2014 | O'Connor |
| 8,716,669 | B2 | 5/2014 | Myaoka et al. |
| 8,767,917 | B2 | 7/2014 | Ruchala et al. |
| 9,283,403 | B2 | 3/2016 | Mazin et al. |
| 9,421,397 | B2 | 8/2016 | Purdie et al. |
| 9,649,509 | B2 | 5/2017 | Mazin et al. |
| 9,694,208 | B2 | 7/2017 | Mazin et al. |
| 9,731,148 | B2 | 8/2017 | Olivera et al. |
| 9,764,161 | B2 | 9/2017 | Mazin et al. |
| 9,782,607 | B2 | 10/2017 | Wiersma et al. |
| 10,143,857 | B2 | 12/2018 | Mazin et al. |
| 10,159,852 | B2 | 12/2018 | Mazin et al. |

(56) References Cited

U.S. PATENT DOCUMENTS

| | | |
|---|---|---|
| 10,617,890 B2 | 4/2020 | Mazin et al. |
| 10,688,320 B2 | 6/2020 | Voronenko et al. |
| 10,695,583 B2 | 6/2020 | Mazin et al. |
| 2002/0051513 A1 | 5/2002 | Pugachev et al. |
| 2002/0163994 A1 | 11/2002 | Jones |
| 2003/0036700 A1 | 2/2003 | Weinberg |
| 2003/0128801 A1 | 7/2003 | Eisenberg et al. |
| 2004/0024300 A1 | 2/2004 | Graf |
| 2004/0096033 A1 | 5/2004 | Seppi et al. |
| 2004/0158416 A1 | 8/2004 | Slates |
| 2005/0068488 A1 | 3/2005 | Tajima |
| 2005/0111621 A1 | 5/2005 | Riker et al. |
| 2005/0207531 A1 | 9/2005 | Dempsey et al. |
| 2005/0216266 A1 | 9/2005 | Gong et al. |
| 2006/0002511 A1 | 1/2006 | Miller et al. |
| 2006/0113482 A1 | 6/2006 | Pelizzari et al. |
| 2006/0159220 A1 | 7/2006 | Heuscher |
| 2006/0173294 A1 | 8/2006 | Ein-Gal |
| 2006/0256915 A1 | 11/2006 | Otto et al. |
| 2006/0293583 A1 | 12/2006 | Saracen et al. |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0075273 A1 | 4/2007 | Birgy et al. |
| 2007/0085012 A1 | 4/2007 | Thompson |
| 2007/0211857 A1 | 9/2007 | Urano et al. |
| 2007/0221869 A1 | 9/2007 | Song |
| 2007/0242801 A1 | 10/2007 | Mackie et al. |
| 2007/0265528 A1 | 11/2007 | Xu et al. |
| 2008/0002811 A1 | 1/2008 | Allison |
| 2008/0008291 A1 | 1/2008 | Alakuijaia et al. |
| 2008/0031404 A1 | 2/2008 | Khamene et al. |
| 2008/0071131 A1 | 3/2008 | Rietzel |
| 2008/0128631 A1 | 6/2008 | Suhami |
| 2008/0156993 A1 | 7/2008 | Weinberg et al. |
| 2008/0230705 A1 | 9/2008 | Rousso et al. |
| 2009/0003655 A1 | 1/2009 | Wollenweber |
| 2009/0116616 A1 | 5/2009 | Lu et al. |
| 2009/0169082 A1 | 7/2009 | Mizuta et al. |
| 2009/0256078 A1 | 10/2009 | Mazin |
| 2010/0040197 A1 | 2/2010 | Maniawski et al. |
| 2010/0051824 A1 | 3/2010 | Nord et al. |
| 2010/0054411 A1 | 3/2010 | Nord et al. |
| 2010/0054412 A1 | 3/2010 | Brinks et al. |
| 2010/0054413 A1 | 3/2010 | Sobering et al. |
| 2010/0067660 A1 | 3/2010 | Maurer, Jr. et al. |
| 2010/0069742 A1 | 3/2010 | Partain et al. |
| 2010/0074408 A1 | 3/2010 | Bert et al. |
| 2010/0150309 A1 | 6/2010 | Nord et al. |
| 2010/0166274 A1 | 7/2010 | Busch et al. |
| 2010/0177871 A1 | 7/2010 | Nord |
| 2010/0232572 A1 | 9/2010 | Nord et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0122997 A1 | 5/2011 | Lu et al. |
| 2011/0272600 A1 | 11/2011 | Bert et al. |
| 2011/0282181 A1 | 11/2011 | Wang et al. |
| 2011/0291015 A1 | 12/2011 | Mazin |
| 2011/0301449 A1 | 12/2011 | Maurer, Jr. |
| 2011/0309255 A1 | 12/2011 | Bert et al. |
| 2011/0313231 A1 | 12/2011 | Guertin et al. |
| 2012/0165652 A1 | 6/2012 | Dempsey |
| 2012/0230464 A1 | 9/2012 | Ling et al. |
| 2013/0083004 A1 | 4/2013 | Nord et al. |
| 2013/0101156 A1 | 4/2013 | Holt |
| 2013/0102830 A1 | 4/2013 | Otto |
| 2013/0177135 A1 | 7/2013 | Boettger et al. |
| 2013/0181711 A1 | 7/2013 | Chaari et al. |
| 2013/0188856 A1 | 7/2013 | Adler, Jr. et al. |
| 2013/0197878 A1 | 8/2013 | Fiege et al. |
| 2013/0266116 A1 | 10/2013 | Abenaim et al. |
| 2013/0289332 A1 | 10/2013 | Purdie et al. |
| 2013/0324784 A1 | 12/2013 | Fredriksson |
| 2013/0328919 A1 | 12/2013 | Holt |
| 2014/0072109 A1 | 3/2014 | Van Heteren et al. |
| 2014/0107390 A1 | 4/2014 | Brown et al. |
| 2014/0239204 A1 | 8/2014 | Orton et al. |
| 2014/0241485 A1 | 8/2014 | Di Fonzo et al. |
| 2014/0275696 A1 | 9/2014 | Dempsey et al. |
| 2014/0294147 A1 | 10/2014 | Chen et al. |
| 2015/0139526 A1 | 5/2015 | Jeong et al. |
| 2015/0206504 A1 | 7/2015 | Pajak et al. |
| 2015/0302467 A1 | 10/2015 | Marenko |
| 2015/0367143 A1 | 12/2015 | Muraki et al. |
| 2016/0008630 A1 | 1/2016 | Ranganatham et al. |
| 2016/0023019 A1 | 1/2016 | Filiberti et al. |
| 2016/0038767 A1 | 2/2016 | Wiersma et al. |
| 2016/0361566 A1 | 12/2016 | Larkin et al. |
| 2017/0368372 A1 | 12/2017 | Mazin et al. |
| 2018/0001109 A1 | 1/2018 | Mazin et al. |
| 2018/0133518 A1 | 5/2018 | Harper et al. |
| 2018/0345042 A1 | 12/2018 | Voronenko et al. |
| 2019/0001152 A1 | 1/2019 | O'Connor et al. |
| 2019/0083815 A1 | 3/2019 | Mazin et al. |
| 2019/0091487 A1 | 3/2019 | Pal et al. |
| 2019/0118001 A1 | 4/2019 | Mazin et al. |
| 2019/0255362 A1 | 8/2019 | Voronenko et al. |
| 2020/0222724 A1 | 7/2020 | Mazin et al. |

FOREIGN PATENT DOCUMENTS

| | | |
|---|---|---|
| CN | 101970043 A | 2/2011 |
| CN | 103505819 A | 1/2014 |
| CN | 204143239 U | 2/2015 |
| CN | 104640205 A | 5/2015 |
| CN | 104866928 A | 8/2015 |
| CN | 104954772 A | 9/2015 |
| CN | 104994909 A | 10/2015 |
| DE | 10 2008 053321 A1 | 5/2010 |
| EP | 0 212 135 B1 | 9/1991 |
| EP | 2 188 815 B1 | 5/2010 |
| EP | 2 687 259 A1 | 1/2014 |
| JP | 09-33658 A | 2/1997 |
| JP | 9-189769 A2 | 7/1997 |
| JP | 2000-105279 A | 4/2000 |
| JP | 2001-340474 A | 12/2001 |
| JP | 2003-534823 A | 11/2003 |
| JP | 2004-513735 A | 5/2004 |
| JP | 2006-145281 A | 6/2006 |
| JP | 2011-514213 A | 5/2011 |
| WO | WO-2000/015299 A1 | 3/2000 |
| WO | WO-2005/031629 A1 | 4/2005 |
| WO | WO-2008/011725 A1 | 1/2008 |
| WO | WO-2009/111580 A2 | 9/2009 |
| WO | WO-2009/111580 A3 | 9/2009 |
| WO | WO-2009/114117 A2 | 9/2009 |
| WO | WO-2009/114117 A3 | 9/2009 |
| WO | WO-2010/015358 A1 | 2/2010 |
| WO | WO-2012/135771 A1 | 10/2012 |
| WO | WO-2014/167461 A1 | 10/2014 |
| WO | WO-2014/181204 A2 | 11/2014 |
| WO | WO-2014/181204 A3 | 11/2014 |
| WO | WO-2014/191204 A1 | 12/2014 |
| WO | WO-2015/150575 A1 | 10/2015 |
| WO | WO-2015/168431 A1 | 11/2015 |
| WO | WO-2015/184549 A1 | 12/2015 |
| WO | WO-2016/001046 A1 | 1/2016 |
| WO | WO-2016/015163 A1 | 2/2016 |
| WO | WO-2016/023786 A1 | 2/2016 |
| WO | WO-2018/183748 A1 | 10/2018 |

OTHER PUBLICATIONS

Bangert, M. et al. (2016). "Accelerated iterative beam angle selection in IMRT," Medical Physics 43.3:1073-1082.

Beck, A. et al. (2009). "Fast gradient-based algorithms for constrained total variation image denoising and deblurring problems," Image Processing, IEEE Transactions on 18:2419-2434.

Beck, A. et al. (2009). "A fast iterative shrinkage-thresholding algorithm for linear inverse problems. SIAM journal on imaging sciences," 2:183-202.

(56) References Cited

OTHER PUBLICATIONS

Beck, A. et al. (2009). "Gradient-based algorithms with applications to signal recovery," Convex Optimization in Signal Processing and Communications, pp. 42-88.
Becker, S. et al. (2011). "Nesta: a fast and accurate first-order method for sparse recovery. SIAM Journal on Imaging Sciences," 4:1-39.
Boyd, S. et al. (2004). Convex optimization. Cambridge university press, 2004.
Censor, Y. et al. (2006). "A unified approach for inversion problems in intensity-modulated radiation therapy," Physics in Medicine and Biology 51:2353.
Chambolle, A. et al. (2011). "A first-order primal-dual algorithm for convex problems with applications to imaging," Journal of Mathematical Imaging and Vision 40:120-145.
Chen, X. et al. (2012). "Smoothing proximal gradient method for general structured sparse regression," The Annals of Applied Statistics 6:719-752.
Combettes, P.L. et al. (2011). "Proximal splitting methods in signal processing," In Fixed-point algorithms for inverse problems in science and engineering, pp. 185-212. Springer.
Combettes, P.L. et al. (2005). "Signal recovery by proximal forward-backward splitting," Multiscale Modeling & Simulation, 4:1168-1200.
Condat, L. (2013). "A primal-dual splitting method for convex optimization involving lipschitzian, proximable and linear composite terms," Journal of Optimization Theory and Applications 158:460-479.
Dieterich, S. et al. (2003). "Skin respiratory motion tracking for stereotactic radiosurgery using the CyberKnife," Elsevier Int'l Congress Series 1256:130-136.
Extended European Search Report dated Oct. 7, 2015, for European Application No. 12 763 280.0, filed on Mar. 30, 2012, 11 pages.
Extended European Search Report dated Nov. 21, 2016, for European Application No. 18 168 947.2, filed on Mar. 30, 2012, 8 pages.
Fan, Q. et al. (2013). "Towards a Planning Scheme for Emission Guided Radiation Therapy (EGRT): FDG Based Tumor Tracking in a Metastatic Breast Cancer Patient," Med. Phys. 40(8):081708, 12 pages.
Final Office Action dated Aug. 2, 2016, for U.S. Appl. No. 15/684,710, filed Aug. 23, 2017, 8 pages.
Gao, H. (2015). "Robust fluence map optimization via alternating direction method of multipliers with automatic parameter optimization," AAPM 2015 talk.
Gibbons, J.P. (2004). "Dose calculation and verification for tomotherapy," 2004 ACMP Meeting, Scottsdale, AZ., 71 total pages.
Goldstein, T. et al. (2009). "The split Bregman method for L1-regularized problems," SIAM Journal on Imaging Sciences 2:323-343.
Handsfield, L.L. et al. (2014). "Phantomless patient-specific TomoTherapy QA via delivery performance monitoring and a secondary Monte Carlo dose calculation," Med. Phys. 41:101703-1-101703-9.
Hindi, H. (2013). "A tutorial on optimization methods for cancer radiation treatment planning," In American Control Conference (ACC), pp. 6804-6816. IEEE.
International Search Report dated Jul. 20, 2012, for PCT Patent Application No. PCT/US2012/31704, filed on Mar. 30, 2012, 2 pages.
International Search Report dated Jun. 27, 2017, for PCT Patent Application No. PCT/US2017/021647, filed on Mar. 9, 2017, 3 pages.
International Search Report dated Jan. 17, 2018, for PCT Application No. PCT/US2017/061728, filed on Nov. 15, 2017, 2 pages.
International Search Report dated Oct. 3, 2018, for PCT Application No. PCT/US2018/035188, filed on May 30, 2018, 4 pages.
Japanese Office Action dated Dec. 25, 2015, for Japanese Patent Application No. 2014-502881 filed Mar. 20, 2012, 14 pages (with English translation).
Kapatoes, J.M. et al. (2001). "A feasible method for clinical delivery verification and dose reconstruction in tomotherapy," Med. Phys. 28:528-542.
Kapatoes, J. M. (2001). "On the accuracy and effectiveness of dose reconstruction for tomotherapy," Physics in Med. Biol. 46:943-966.
Keall, P .J. et al. (2001). "Motion adaptive x-ray therapy: a feasibility study," Physics in Med. Biol. 46:1-10.
Lu, W. (2008). "Real-time motion-adaptive delivery (MAD) using binary MLC: I. Static beam (topotherapy) delivery," Phys. Med. Biol. 53:6491-6511.
Lu, W. (2009). "Real-time motion-adaptive-optimization (MAO) in tomotherapy," Phys. Med. Biol. 54:4373-4398.
McMahon, R. et al. (2008). "A real-time dynamic-MLC control algorithm for delivering IMRT to targets undergoing 2D rigid motion in the beam's eye view," Med. Phys. 35:3875-3888.
Nesterov, Y. (1983). "A method of solving a convex programming problem with convergence rate $O(1/k2)$," In Soviet Mathematics Doklady, vol. 27, pp. 372-376.
Nesterov, Y. (2004). "Introductory lectures on convex optimization," vol. 87. Springer Science & Business Media.
Nesterov, Y. (2005). "Smooth minimization of non-smooth functions," Mathematical programming 103:127-152.
Nesterov, Y. (2007). Gradient methods for minimizing composite objective function.
Non-Final Office Action dated Feb. 24, 2017, for U.S. Appl. No. 15/069,390, filed Mar. 14, 2016, 6 pages.
Non-Final Office Action dated Feb. 21, 2018, for U.S. Appl. No. 15/684,710, filed Aug. 23, 2017, 10 pages.
Non-Final Office Action dated Mar. 27, 2018, for U.S. Appl. No. 15/684,693, filed Aug. 23, 2017, 7 pages.
Notice of Allowance dated May 18, 2017, for U.S. Appl. No. 15/069,390, filed Mar. 14, 2016, 5 pages.
Notice of Allowance dated Jul. 19, 2017, for U.S. Appl. No. 15/499,671, filed Apr. 27, 2017, 8 pages.
Notice of Allowance dated Oct. 3, 2018, for U.S. Appl. No. 15/684,693, filed Aug. 23, 2017, 5 pages.
Notice of Allowance dated Oct. 25, 2018, for U.S. Appl. No. 15/684,710, filed Aug. 23, 2017, 7 pages.
Nguyen, D. et al. (2015). "Dose domain regularization of MLC leaf patterns for highly complex IMRT plans," Medical Physics 42:1858-1870.
Nguyen, D. et al. (2015). "A new intensity modulation radiation therapy (IMRT) optimizer solution with robust fluence maps for MLC segmentation," Medical physics 42:3740.
Nguyen, D. et al. (2015). "A novel Haar wavelet based approach to deliver non-coplanar intensity modulated radiotherapy using sparse orthogonal collimators," Medical physics 42:3532-3532.
Oiivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," J. Cancer Sci. Ther: 2:145-152.
Parikh, N. et al. (2013). "Proximal algorithms," Foundations and Trends in Optimization 1:123-231.
Parikh, N. et al. (2014). "Block splitting for distributed optimization," Mathematical Programming Computation 6:77-102.
Rockafellar, R.T. (1967). "Duality and stability in extremum problems involving convex functions," Pacific Journal of Mathematics 21:167-187.
Romeijn, H. et al. (2005). "A column generation approach to radiation therapy treatment planning using aperture modulation," SIAM Journal on Optimization 15.3:838-862.
Rudin, L. et al. (1992). "Nonlinear total variation based noise removal algorithms," Physica D: Nonlinear Phenomena, 60(1):259-268.
Salari, E. (2013). "Mathematical optimization in radiotherapy treatment planning," Department of Radiation Oncology Massachusetts General Hospital and Harvard Medical School, Presentation, 80 total pages.

(56) References Cited

OTHER PUBLICATIONS

Scheinberg, K. (2014). "Fast first-order methods for composite convex optimization with backtracking," Foundations of Computational Mathematics 14:389-417.
The Partial Supplementary European Search Report, dated Jun. 25, 2015 for European Application No. 12763280.0, filed on Mar. 30, 2012, 6 pages.
Tseng, P. (2008). "On accelerated proximal gradient methods for convex-concave optimization," SIAM J, Optim., pp. 1-20.
Voet, P. et al. (2013). "Toward fully automated multicriterial plan generation: A prospective clinical study," International Journal of Radiation Oncology* Biology* Physics 85:866-872.
Written Opinion dated Jul. 20, 2012, for PCT Patent Application No. PCT/US2012/31704, filed on Mar. 30, 2012, 10 pages.
Written Opinion of the International Searching Authority dated Jun. 27, 2017, for PCT Patent Application No. PCT/US2017/021647, filed on Mar. 9, 2017, 5 pages.
Written Opinion of the International Searching Authority dated Jan. 17, 2018, for PCT Application No. PCT/US2017/061728, filed on Nov. 15, 2017, 7 pages.
Written Opinion of the International Searching Authority dated Oct. 3, 2018, for PCT Application No. PCT/US2018/035188, filed on May 30, 2018, 28 pages.
Yan, D. et al. (1997). "Adaptive radiation therapy," *Physics Med. Biol.* 42:123-132.
Zarepisheh, M. et al. (2015). "An integrated alternating direction method of multipliers for treatment planning optimization," AAPM 2015 talk.
Chang, J.Y. et al. (2008). "Image-Guided Radiation Therapy for Non-Small Cell Lung Cancer," *J. Thorac. Oncol. FEB* 3(2):177-186.
Erdi, Y.E. (Feb. 2007). "The Use of PET for Radiotherapy," *Current Medical Imaging Reviews* 3(1):3-16.
Extended European Search Report dated Oct. 15, 2019, for European Application No. 17 764 132.1, filed on Mar. 9, 2017, 4 pages.
Fan, Q. (Nov. 2012). "Emission Guided Radiation Therapy for Lung and Prostrate Cancers: A Feasibility Study on a Digital Patient," *Med. Phys.* 39(11):7140-7152.
Hunt, M.A. et al. (2003). "Treatment Planning Considerations using IMRT," pp. 103-121.
International Search Report dated Jun. 14, 2019, for PCT Application No. PCT/US2019/017855, filed on Feb. 13, 2019, 4 pages.
International Search Report dated Apr. 23, 2020, for PCT Application No. PCT/US2020/013927, filed on Jan. 16, 2020, 3 pages.
Lee, S. et al. (2015). "Treatment plan comparison of Linac step and shoot, tomotherapy, RapidArc, and proton therapy for prostate cancer using dosimetrical and biological index," J. Korean Physical Society 67:7-16 (with tables 1-5), 28 total pages.
Mackie, T.R. et al. (Nov.-Dec. 1993). "Tomotherapy: A New Concept for the Delivery of Dynamic Conformal Radiotherapy," *Med. Phys.* 20(6):1709-1719.
Mazin, S.R. et al. (Dec. 2010). "Emission-Guided Radiation Therapy: Biologic Targeting and Adaptive Treatment," *Journal of American College of Radiology* 7(12):989-990.
Non-Final Office Action dated Aug. 30, 2019, for U.S. Appl. No. 16/193,725, filed Nov. 16, 2018, 5 pages.
Non-Final Office Action dated Sep. 19, 2019, for U.S. Appl. No. 16/217,417, filed Dec. 12, 2018, 7 pages.
Non-Final Office Action dated Dec. 6, 2019, for U.S. Appl. No. 15/993,325, filed May 30, 2018, 8 pages.
Notice of Allowance dated Jan. 21, 2020, for U.S. Appl. No. 16/193,725, filed Nov. 16, 2018, 11 pages.
Notice of Allowance dated Mar. 13, 2020, for U.S. Appl. No. 16/217,417, filed Dec. 12, 2018, 6 pages.
Notice of Allowance dated Apr. 20, 2020, for U.S. Appl. No. 15/993,325, filed May 30, 2018, 7 pages.
Written Opinion of the International Searching Authority dated Jun. 14, 2019, for PCT Application No. PCT/US2019/017855, filed on Feb. 13, 2019, 10 pages.
Written Opinion of the International Searching Authority dated Apr. 23, 2020, for PCT Application No. PCT/US2020/013927, filed on Jan. 16, 2020, 4 pages.
Yamaya, T. et al. (Jan. 14, 2008). "A Proposal of an Open PET Geometry," *Physics in Medicine and Biology* 53:757-773.

\* cited by examiner

TABLE 1: PENALTY Functions

| Description | $\Gamma(v)$ | $\text{prox}_{t\Gamma}(v)$ |
|---|---|---|
| One-sided $L_1$-penalty | $\mu\|(v-\ell)_-\|_1$ | $v - P_{[-\mu t, 0]}(v-\ell)$ |
| One-sided $L_2$-penalty | $\frac{\mu}{2}\|(v-\ell)_-\|_2^2$ | $p_j = \begin{cases} \frac{v_j + \mu t \ell_j}{1+\mu t} & \text{if } v_j < \ell_j \\ v_j & \text{otherwise} \end{cases}$ |
| Indicator penalty | $I_{\geq \ell}(v)$ | $\max(v, \ell)$ |

| | $\Phi_i(y_i)$ | $\text{prox}_{t\Phi_i}(y_i)$ |
|---|---|---|
| One-sided $L_1$-penalty | $\alpha_i\|(y_i - u_i)_+\|_1$ | $y_i - P_{[0, \alpha_i t]}(y_i - u_i)$ |
| One-sided $L_2$-penalty | $\frac{\alpha_i}{2}\|(y_i - u_i)_+\|_2^2$ | $p_j = \begin{cases} \frac{y_{i,j} + \alpha_i t u_{i,j}}{1+\alpha_i t} & \text{if } y_{i,j} > u_{i,j} \\ y_{i,j} & \text{otherwise} \end{cases}$ |
| One-sided $L_1$-penalty + quadratic | $\alpha_i\|(y_i - u_i)_+\|_1 + \frac{\beta_i}{2}\|y_i\|_2^2$ | $\frac{y_i}{\beta_i t + 1} - P_{[0, \frac{\alpha_i t}{\beta_i t + 1}]}\left(\frac{y_i}{\beta_i t + 1} - u_i\right)$ |
| Indicator penalty | $I_{\leq u_i}(y_i)$ | $\min(y_i, u_i)$ |

| | $\Psi(y_{N+1})$ | $\text{prox}_{t\Psi}(y_{N+1})$ |
|---|---|---|
| $L_1$-penalty | $\eta\|y_{N+1}\|_1$ | $y_{N+1} - P_{[-\eta t, \eta t]}(y_{N+1})$ |
| $L_2$-penalty | $\frac{\eta}{2}\|y_{N+1}\|_2^2$ | $\frac{y_{N+1}}{\eta t + 1}$ |
| Indicator penalty | $I_{[-\eta, \eta]}(y_{N+1})$ | $P_{[-\eta, \eta]}(y_{N+1})$ |

| | $\Theta(x)$ | $\text{prox}_{t\Theta}(x)$ |
|---|---|---|
| Indicator penalty | $I_{\geq 0}(x)$ | $\max(x, 0)$ |
| Indicator + $L_1$-penalty | $I_{\geq 0}(x) + \epsilon\|x\|_1$ | $\max(x - \epsilon t \mathbf{1}, 0)$ |
| Indicator + $L_2$-penalty | $I_{\geq 0}(x) + \frac{\epsilon}{2}\|x\|_2^2$ | $\max\left(\frac{x}{\epsilon t + 1}, 0\right)$ |

FIG. 2

TABLE 2: Notation and Definitions

| Notation | Definition |
|---|---|
| $x_+$ | $\max(x, 0)$ = vector whose $j$th component is $\max(x_j, 0)$ |
| $x_-$ | $\max(-x, 0)$ = vector whose $j$th component is $\max(-x_j, 0)$. |
| $I_C(x)$ | $\begin{cases} 0 & \text{if } x \in C \\ \infty & \text{otherwise} \end{cases}$ |
| $I_{[a,b]}(x)$ | $\begin{cases} 0 & \text{if } a \leq x_j \leq b \text{ for } j = 1, \ldots, m \\ \infty & \text{otherwise} \end{cases}$ |
| $I_{\geq \ell}(x)$ | $\begin{cases} 0 & \text{if } x_j \geq \ell_j \text{ for } j = 1, \ldots, m \\ \infty & \text{otherwise} \end{cases}$ |
| $P_C(x)$ | $\arg\min_u \|u - x\|_2$ = projection of $x$ onto $C$ |
| $P_{[a,b]}(x)$ | projection of $x$ onto $[a,b]^m = \{x \mid a \leq x_j \leq b \text{ for } j = 1, \ldots, m\}$ |
| $P_{\geq \ell}(x)$ | $\max(x, \ell)$ = projection of $x$ onto $\{y \in \mathbb{R}^n \mid y \geq \ell\}$ |
| $f^*(z)$ | $\sup_x \langle z, x \rangle - f(x)$ |
| $\text{prox}_{tf}(x)$ | $\arg\min_u f(u) + \frac{1}{2t}\|u - x\|_2^2$ |
| $f^{(t)}(x)$ | $\min_u f(u) + \frac{1}{2t}\|u - x\|_2^2$ |

FIG. 3

TABLE 3: Prox-operator calculus rules

| $g(x)$ | $\mathrm{prox}_{tg}(x)$ | |
|---|---|---|
| $\sum_{k=1}^{K} f_k(x_k)$ | $(\mathrm{prox}_{tf_1}(x_1), \ldots, \mathrm{prox}_{tf_K}(x_K))$ | (3.1) |
| $cf(x - x_0)$ | $\mathrm{prox}_{ctf}(x - x_0) + x_0$ | (3.2) |
| $f^*(x)$ | $x - t\mathrm{prox}_{(1/t)f}(x/t)$ | (3.3) |
| $I_C(x)$ | $P_C(x) = $ projection of $x$ onto $C$ | |
| $I_{\geq 0}(x)$ | $x_+ = \max(x, 0)$ | |
| $\|x\|$ | $x - tP_B(x)$, where $B$ is dual norm unit ball | |
| $\|x\|_1$ | $x - P_{[-t,t]}(x)$ | |
| $\|x_+\|_1$ | $x - P_{[0,t]}(x)$ | (3.4) |
| $\|x_-\|_1$ | $x - P_{[-t,0]}(x)$ | (3.5) |
| $\frac{1}{2}\|x\|_2^2$ | $x/(1+t)$ | |
| $\frac{1}{2}\|x_+\|_2^2$ | $p_j = \begin{cases} x_j/(1+t) & \text{if } x_j > 0 \\ x_j & \text{otherwise} \end{cases}$ | |
| $\frac{1}{2}\|x_-\|_2^2$ | $p_j = \begin{cases} x_j/(1+t) & \text{if } x_j < 0 \\ x_j & \text{otherwise} \end{cases}$ | |

FIG. 4

Algorithm 1 Proximal gradient method with fixed step size

Initialize $x_0$
for $k = 1, 2, \ldots$ do
$\quad x_k := \text{prox}_{tg}(x_{k-1} - t\nabla f(x_{k-1}))$
end for

FIG. 5

Algorithm 2 Proximal gradient method with line search

Initialize $x_0$ and $t_0 > 0$
for $k = 1, 2, \ldots$ do
$\quad t := t_{k-1}/r$
$\quad$ repeat
$\quad\quad x := \text{prox}_{tg}(x_{k-1} - t\nabla f(x_{k-1}))$
$\quad\quad$ break if $f(x) \leq f(x_{k-1}) + \langle \nabla f(x_{k-1}), x - x_{k-1}\rangle + \frac{1}{2t}\|x - x_{k-1}\|_2^2$
$\quad\quad t := rt$
$\quad t_k := t$
$\quad x_k := x$
end for

FIG. 6

Algorithm 3 FISTA with fixed step size

Initialize $x_{(-1)}$, set $x_0 := x_{(-1)}$
for $k = 1, 2, \ldots$ do
$\quad y := x_{k-1} + \frac{k-2}{k+1}(x_{k-1} - x_{k-2})$
$\quad x_k := \text{prox}_{tg}(y - t\nabla f(y))$
end for

FIG. 7

Algorithm 4 FISTA with line search

Initialize $x_0$ and $t_0 > 0$, set $v_0 := x_0$
for $k = 1, 2, \ldots$ do
$\quad t := t_{k-1}/r$
$\quad$ repeat
$\quad\quad \theta := \begin{cases} 1 & \text{if } k = 1 \\ \text{positive root of } t_{k-1}\theta^2 = t\theta_{k-1}^2(1-\theta) & \text{if } k > 1 \end{cases}$
$\quad\quad y := (1-\theta)x_{k-1} + \theta v_{k-1}$
$\quad\quad x := \text{prox}_{tg}(y - t\nabla f(y))$
$\quad\quad \text{break if } f(x) \leq f(y) + \langle \nabla f(y), x-y \rangle + \frac{1}{2t}\|x-y\|_2^2$
$\quad\quad t := rt$
$\quad t_k := t$
$\quad \theta_k := \theta$
$\quad x_k := x$
$\quad v_k := x_{k-1} + \frac{1}{\theta_k}(x_k - x_{k-1})$
end for

FIG. 8

Algorithm 5 Chambolle-Pock algorithm (with overrelaxation)

Initialize $x_0, z_0$
for $k = 1, 2, \ldots$ do
$\quad \bar{x}_k := \text{prox}_{tf}(x_{k-1} - tA^T z_{k-1})$
$\quad \bar{z}_k := \text{prox}_{sg^*}(z_{k-1} + sA(2\bar{x}_k - x_{k-1}))$
$\quad (x_k, z_k) := \rho(\bar{x}_k, \bar{z}_k) + (1-\rho)(x_{k-1}, z_{k-1})$
end for

FIG. 9

FLUENCE MAP GENERATION METHODS FOR RADIOTHERAPY

CROSS-REFERENCE TO RELATED APPLICATIONS

This application is a continuation of International Patent Application Number PCT/US2017/021647, filed on Mar. 9, 2017, which claims priority to U.S. Provisional Patent Application No. 62/305,974, filed on Mar. 9, 2016, each of which is hereby incorporated by reference in its entirety.

BACKGROUND

Fluence map optimization (FMO) problems in radiation treatment planning are most often solved by interior point methods or by gradient-based methods such as the projected gradient method or quasi-Newton methods. In the first approach, the optimization problem is typically reformulated as either a linear program or a quadratic program, which is then solved using an interior point method. While interior point methods perform very well for small and medium-size problems, they have the disadvantage that they require solving a large linear system of equations at each iteration. For large scale problems, including large fluence map optimization problems, this can become prohibitively computationally intensive. Gradient-based methods do not suffer from this limitation; however, they are unable to handle nondifferentiable objective functions and complex constraints. This puts significant restrictions on how the fluence map optimization problem can be formulated, and limits the quality of the resulting treatment plans.

BRIEF SUMMARY

Described herein are methods for generating fluence maps and/or fluence map optimization (FMO) for radiation treatment planning. One variation of a method for FMO comprises a proximal gradient method (e.g., an accelerated proximal gradient method such as FISTA) with a smoothed-out nondifferentiable penalty function to compute a fluence map that may be used by a radiotherapy system to apply a specified dose of radiation to one or more regions of interest (ROI) or volumes of interest (VOI). The fluence map may comprise a set of radiation beamlet data (e.g., beamlet intensity data) derived from a prescribed radiation dose plan (e.g., a treatment plan). The fluence map may be used to position a radiation source at one or more selected angles with respect to the ROI and to adjust the beam intensity of the radiation source such that a desired radiation dose is applied to the ROI, while reducing radiation exposure of organs-at-risk (OAR). The methods described herein may compute a fluence map such that the radiation exposure of OARs is below a preselected threshold, while still delivering a selected dose of radiation to a ROI. Some variations may use one or more $L_1$-type penalty or cost functions, while other variations may use one or more $L_2$-type penalty or cost functions.

Calculating or generating a fluence map for radiation therapy may comprise selecting a volume of interest, selecting a plurality of voxels within the volume of interest, and selecting a set of candidate beamlets $b=\{b_i\}$. A beamlet may be a portion of a full radiation beam that is defined by a multi-leaf collimator leaf opening (e.g., as depicted in FIG. 1B). Each of the plurality of voxels may have an acceptable dose range (e.g., a maximum radiation dose level and a minimum radiation dose level), which may be defined by a treatment plan and/or a clinician. The set of candidate beamlets may have initial beamlet intensity weights $x^0=\{x_i^0\}$. The method may comprise calculating a dose matrix A for the volume of interest based on the set of candidate beamlets b. The dose matrix A represents per-voxel dose delivered to each of the plurality of voxels by the set of candidate beamlets b. One example of a dose calculation matrix A for n candidate beamlets $\{b_i\}$ and for a VOI with k pre-selected voxels is a (k×n) matrix. An i-th column of the dose calculation matrix A (which has k elements) represents a dose contribution from a unity-weighted beamlet $b_i$ to each of the k voxels. Dose matrix A is may be calculated column-by-column, for example, by ray-tracing each beamlet's aperture along the path through the patient's volume and calculating the contribution of a unity-weighted beamlet to each of the k voxels. Several well-known algorithms exist for this dose calculation process, differing in their accuracy and speed. Examples of dose calculation algorithms that may be used in any of the methods described herein may include Monte-Carlo simulation, collapsed-cone convolution superposition, pencil-beam convolution, and others.

A fluence map generation method may also comprise calculating a fluence map having a final set of beamlet intensity weights $x^k$ by adjusting the initial beamlet intensity weights according to a proximal gradient method ($x^{k-1} \rightarrow x^k$) with a penalty function containing one or more linear penalties. The proximal gradient method may be an accelerated proximal gradient method such as fast iterative shrinkage-thresholding algorithm (FISTA). The proximal gradient method may iterate on the initial beamlet intensity weights until the adjusted beamlet intensity weights converge on a final set of beamlet intensity weights such that changes between iterations of the beamlet intensity weights are less than a predetermined residual criterion. More generally, the method may use any proximal methods. Solving an optimization problem involves finding an input value that minimizes or maximizes a real-valued function. When minimization is used, the function is often called a "cost function" or "penalty function". Convex optimization restricts the types of functions to so-called convex functions. Algorithms for convex optimizations guarantee convergence to a global minima, and may have other useful properties. A proximal algorithm or method is an algorithm for solving a convex optimization problem, and may be, in fluence map generation for example, an algorithm for minimizing a convex penalty function. Proximal algorithms use proximal operators of the components of the penalty functions. Evaluating a proximal operator of a function involves solving a small convex optimization problem. For these small sub-problems, a closed form solution usually exists, making the overall algorithm efficient. A proximal gradient algorithm is one example of a proximal algorithm, and it assumes that a cost or penalty function can be split as f(x)+g(x), where f(x) is differentiable and g(x) has a simple closed form of the proximal operator. For radiotherapy fluence map optimization and/or fluence map generation, the optimization problem involves multiple beamlets and multiple voxels, but the penalty function must be a scalar real-valued function. A penalty function (or cost function) that is typically used may include a sum of multiple components, where each component directs the iterative process to a solution to satisfy a specific problem goal. In the case of radiation therapy, the problem goal to be satisfied is the prescription target dose for a VOI (or a plurality of VOIs) in a patient. Each component in turn may also a summation across multiple beamlets of multiple voxels. A common choice for a penalty function component is a $L_2$ penalty, also known as a quadratic penalty. A quadratic penalty or cost function is a sum of squares, for instance $sum_i (d_i^2)$ is a penalty that would tend to minimize overall dose. Some components of a penalty or cost function may be a $L_1$ penalty, also known as a linear penalty, which is a simple sum, for example $sum_i (d_i)$. A penalty or cost function may comprise one or more $L_1$ penalties and/or one or more $L_2$ penalties. An accelerated proximal gradient method may include addition terms (such as a momentum term) to help direct and/or speed up (i.e., increase the rate of, decrease the number of iterations) convergence to a solution set.

Generating or calculating a fluence map may comprise smoothing the penalty function such that it is differentiable. For example, the penalty function may be smoothed using Moreau-Yosida regularization. The initial set of beamlet intensity weights $\{x^0\}$ is an all-zero vector. The beamlets in the set of candidate beamlets b are divided between a smaller set of firing positions or angles $\{f_i\}$. A firing position is a location where a radiation source may be positioned (e.g., relative to a patient region) to fire a beamlet. In a radiation therapy system where the radiation source is mounted on a circular rotatable gantry, a firing position may be a firing angle and identified by the locations around the circular gantry (from 0 to 360 degrees) around a patient treatment area. For example, the set of firing angles $\{f_i\}$ may comprise a plurality of angles around a patient area of a radiation treatment device. The plurality of firing angles may be evenly distributed 360 degrees around the patient area.

Any of the proximal gradient method penalty functions described herein may comprise one or more quadratic or $L_2$ penalties. Penalty functions may penalize voxel dose excursions outside of the acceptable dose range. That is, as part of a proximal gradient method iteration, the magnitude of the dose deviation outside of the acceptable dose range is incorporated into the calculation of a set of beamlet weights. Such penalty functions may discourage beamlets that result in a dose delivery to a voxel or VOI that is not within the acceptable dose range. Some methods may have a penalty function that comprises a single-value penalty function that aggregates the voxel dose excursions outside of the acceptable dose range of all of the voxels in the volume of interest. The acceptable dose range of each of the plurality of voxels may be determined at least in part by a treatment plan.

Fluence map generation or calculation may comprise selecting a second volume of interest, selecting a second plurality of voxels within the second volume of interest where each of the voxels has an acceptable dose range, and calculating the dose matrix A to include the second volume of interest and second plurality of voxels. That is, the dose matrix A may represent per-voxel dose delivered to each of the first and second plurality of voxels by the set of candidate beamlets b. Optionally, some methods may comprise segmenting a fluence map into a set of multi-leaf collimator and radiation source positioning instructions.

Also described herein is a system for calculating or generating a fluence map for radiation therapy. A system may comprise a processor that configured to select a volume of interest, select a plurality of voxels within the volume of interest, where each of the voxels has an acceptable dose range, select a set of candidate beamlets $b=\{b_i\}$ having initial beamlet intensity weights $x^0=\{x_i^0\}$, calculate a dose matrix A for the volume of interest based on the set of candidate beamlets b, where the dose matrix A represents per-voxel dose delivered to each of the plurality of voxels by the set of candidate beamlets b, and calculate a fluence map comprising a final set of beamlet intensity weights $x^k$ by adjusting the initial beamlet intensity weights according to an proximal gradient method update ($x^{k-1} \rightarrow x^k$) with a penalty function containing one or more linear penalties that iterates on the initial beamlet intensity weights until the adjusted beamlet intensity weights converge on a final set of beamlet intensity weights such that changes between iterations of the beamlet intensity weights are less than a predetermined residual criterion. The processor may also be configured to store the fluence map in a processor memory. A beamlet may be a portion of a full radiation beam that is defined by a multi-leaf collimator leaf opening (e.g., as depicted in FIG. 1B). Each of the plurality of voxels may have an acceptable dose range (e.g., a maximum radiation dose level and a minimum radiation dose level), which may be defined by a treatment plan and/or a clinician. The set of candidate beamlets may have initial beamlet intensity weights $x^0=\{x_i^0\}$. The dose matrix A represents per-voxel dose delivered to each of the plurality of voxels by the set of candidate beamlets b. One example of a dose calculation matrix A for n candidate beamlets $\{b_i\}$ and for a VOI with k pre-selected voxels is a (k×n) matrix. An i-th column of the dose calculation matrix A (which has k elements) represents a dose contribution from a unity-weighted beamlet $b_i$ to each of the k voxels. Dose matrix A is may be calculated column-by-column, for example, by ray-tracing each beamlet's aperture along the path through the patient's volume and calculating the contribution of a unity-weighted beamlet to each of the k voxels. Several well-known algorithms exist for this dose calculation process, differing in their accuracy and speed. Examples of dose calculation algorithms that may be used in any of the methods described herein may include Monte-Carlo simulation, collapsed-cone convolution superposition, pencil-beam convolution, and others.

A system processor may be configured to iterate on a proximal gradient method that may be an accelerated proximal gradient method such as fast iterative shrinkage-thresholding algorithm (FISTA). The proximal gradient method may iterate on the initial beamlet intensity weights until the adjusted beamlet intensity weights converge on a final set of beamlet intensity weights such that changes between iterations of the beamlet intensity weights are less than a predetermined residual criterion. More generally, the method may use any proximal methods. Solving an optimization problem involves finding an input value that minimizes or maximizes a real-valued function. When minimization is used, the function is often called a "cost function" or "penalty function". Convex optimization restricts the types of functions to so-called convex functions. Algorithms for convex optimizations guarantee convergence to a global minima, and may have other useful properties. A proximal algorithm or method is an algorithm for solving a convex optimization problem, and may be, in fluence map generation for example, an algorithm for minimizing a convex penalty function. Proximal algorithms use proximal operators of the components of the penalty functions. Evaluating a proximal operator of a function involves solving a small convex optimization problem. For these small sub-problems, a closed form solution usually exists, making the overall algorithm efficient. A proximal gradient algorithm is one example of a proximal algorithm, and it assumes that a cost or penalty function can be split as f(x)+g(x), where f(x) is differentiable and g(x) has a simple closed form of the proximal operator. For radiotherapy fluence map optimization and/or fluence map generation, the optimization problem involves multiple beamlets and multiple voxels, but the penalty function must be a scalar real-valued function. A penalty function (or cost function) that is typically used may include a sum of multiple components, where each component directs the iterative process to a solution to satisfy a specific problem goal. In the case of radiation therapy, the problem goal to be satisfied is the prescription target dose for a VOI (or a plurality of VOIs) in a patient. Each component in turn may also a summation across multiple beamlets of multiple voxels. A common choice for a penalty function component is a $L_2$ penalty, also known as a quadratic penalty. A quadratic penalty or cost function is a sum of squares, for instance $sum_i (d_i^2)$ is a penalty that would tend to minimize overall dose. Some components of a penalty or cost function may be a $L_1$ penalty, also known as a linear penalty, which is a simple sum, for example $sum_i (d_i)$. A penalty or cost function may comprise one or more $L_1$ penalties and/or one or more $L_2$ penalties. An accelerated proximal gradient method may include addition terms (such as a momentum term) to help direct and/or speed up (i.e., increase the rate of, decrease the number of iterations) convergence to a solution set.

Some processors configured for generating a fluence map may be configured to smooth out the penalty function such that it is differentiable. For example, the penalty function may be smoothed using Moreau-Yosida regularization. The initial set of beamlet intensity weights $\{x^0\}$ is an all-zero vector. The beamlets in the set of candidate beamlets b are divided between a smaller set of firing positions or angles $\{f_i\}$. A firing position is a location where a radiation source may be positioned (e.g., relative to a patient region) to fire a beamlet. In a radiation therapy system where the radiation source is mounted on a circular rotatable gantry, a firing position may be a firing angle and identified by the locations around the circular gantry (from 0 to 360 degrees) around a patient treatment area. For example, the set of firing angles $\{f_i\}$ may comprise a plurality of angles around a patient area of a radiation treatment device. The plurality of firing angles may be evenly distributed 360 degrees around the patient area.

A system processor configured to generate a fluence map may use any of the proximal gradient method penalty functions described herein with one or more quadratic or $L_2$ penalties. Penalty functions may penalize voxel dose excursions outside of the acceptable dose range. That is, as part of a proximal gradient method iteration, the magnitude of the dose deviation outside of the acceptable dose range is incorporated into the calculation of a set of beamlet weights. Such penalty functions may discourage beamlets that result in a dose delivery to a voxel or VOI that is not within the acceptable dose range. Some methods may have a penalty function that comprises a single-value penalty function that aggregates the voxel dose excursions outside of the acceptable dose range of all of the voxels in the volume of interest. The acceptable dose range of each of the plurality of voxels may be determined at least in part by a treatment plan.

A system for generating a fluence map may comprise a processor configured to select a second volume of interest, select a second plurality of voxels within the second volume of interest where each of the voxels has an acceptable dose range, and calculate the dose matrix A to include the second volume of interest and second plurality of voxels. That is, the dose matrix A may represent per-voxel dose delivered to each of the first and second plurality of voxels by the set of candidate beamlets b. A radiation system may further comprise a multi-leaf collimator disposed in a beam path of the therapeutic radiation source, and the processor may be configured to segment the fluence map into a set of multi-leaf collimator instructions and to transmit the instructions to the radiation therapy system. The radiation therapy system may comprise one or more PET detectors. The therapeutic radiation source of a radiation therapy system may be movable about the patient area at a speed of at least about 40 RPM.

Fluence map generation methods comprising a proximal gradient method with a penalty function (also known as a cost function) having one or more smoothed linear penalties (e.g., regularized $L_1$ penalties) may have advantages over fluence map generation methods that use weighted quadratic penalties. Fluence map generation methods typically use weighted quadratic penalties (e.g., $L_2$ penalties) derived from user-specified dose constraints and weghts as components in an overall penalty function. The use of quadratic penalties to model minimum and maximum dose constraints on voxels, often results in solutions with lots of small magnitude violations of the desired dose constraint (e.g. min-dose, or max-dose or other), and may require users to increase the min-dose or decrease the max-dose parameters in the penalty function beyond what is clinically desired, so that a problem converges to a solution with no violations of the original clinically desired constraints. Alternative strategy that is employed by users is manually tuning the penalty function component weights. Quadratic penalties may also require a greater number of iterations before converging on a set of beamlet weights. In some cases, a fluence map generation method that includes a quadratic penalty or cost function may generate a set of beamlet weights that results in a greater number of violations of user-imposed constraints. In contrast, the fluence map generation methods described herein which comprise a proximal gradient method (such as an accelerated proximal gradient method, for example, FISTA) having linear (e.g., $L_1$ penalty) components in the penalty function may converge on a set of beamlet weights faster (i.e., in fewer iterations), may result in a solution that has fewer violations of clinical dose and other constraints with fewer required interventions (such as weight tuning) by the user, may be simpler and less-computationally intensive to implement in a processor, and/or may be more amenable to parallelization on multi-core CPUs and/or GPUs. A fluence map generation method comprising a proximal gradient method with a penalty or cost function having one or more $L_1$ penalties may promote better plan conformance to user-specified planning goals, i.e., minimum target ROI or VOI dose, maximum OAR dose as compared to methods with a penalty or cost function having one or more $L_2$ penalties.

BRIEF DESCRIPTION OF THE DRAWINGS

FIG. 2 depicts Table 1: Examples of penalty functions.

FIG. 3 depicts Table 2: Notation and Definitions.

FIG. 4 depicts Table 3: Prox-operator calculus rules.

FIG. 5 depicts a variation of a proximal gradient method with fixed step size (Algorithm 1).

FIG. 6 depicts a variation of a proximal gradient method with line search (Algorithm 2).

FIG. 7 depicts a variation of a FISTA method with fixed step size (Algorithm 3).

FIG. 8 depicts a variation of a FISTA method with line search (Algorithm 4).

FIG. 9 depicts a variation of a Chambolle-Pock method with overrelaxation (Algorithm 5).

DETAILED DESCRIPTION

Disclosed herein are methods for generating a fluence map having a set of beamlet intensities and angles that may be used by a radiation therapy system to position a radiation source and to control the intensity of the generated radiation beam such that a selected/prescribed dose of radiation is applied to the ROI (e.g., target volume, irradiation target volume such as tumor regions) while limiting the amount of radiation applied to one or more organs-at-risk or OARs (e.g., irradiation-avoidance volumes). That is, given an image of the patient (e.g., a 3-D digital image) that includes information about the location(s) and shape(s) of the target(s)-to-be-irradiated, prescription dose(s) to the target(s), locations of OARs and dose limits on OARs (as well as other dose constraints), a FMO or fluence map generation method computes a set of beamlet intensities and angles that deliver the prescription dose to the target(s) while meeting OAR dose limits and other constraints.

Figure 1A:
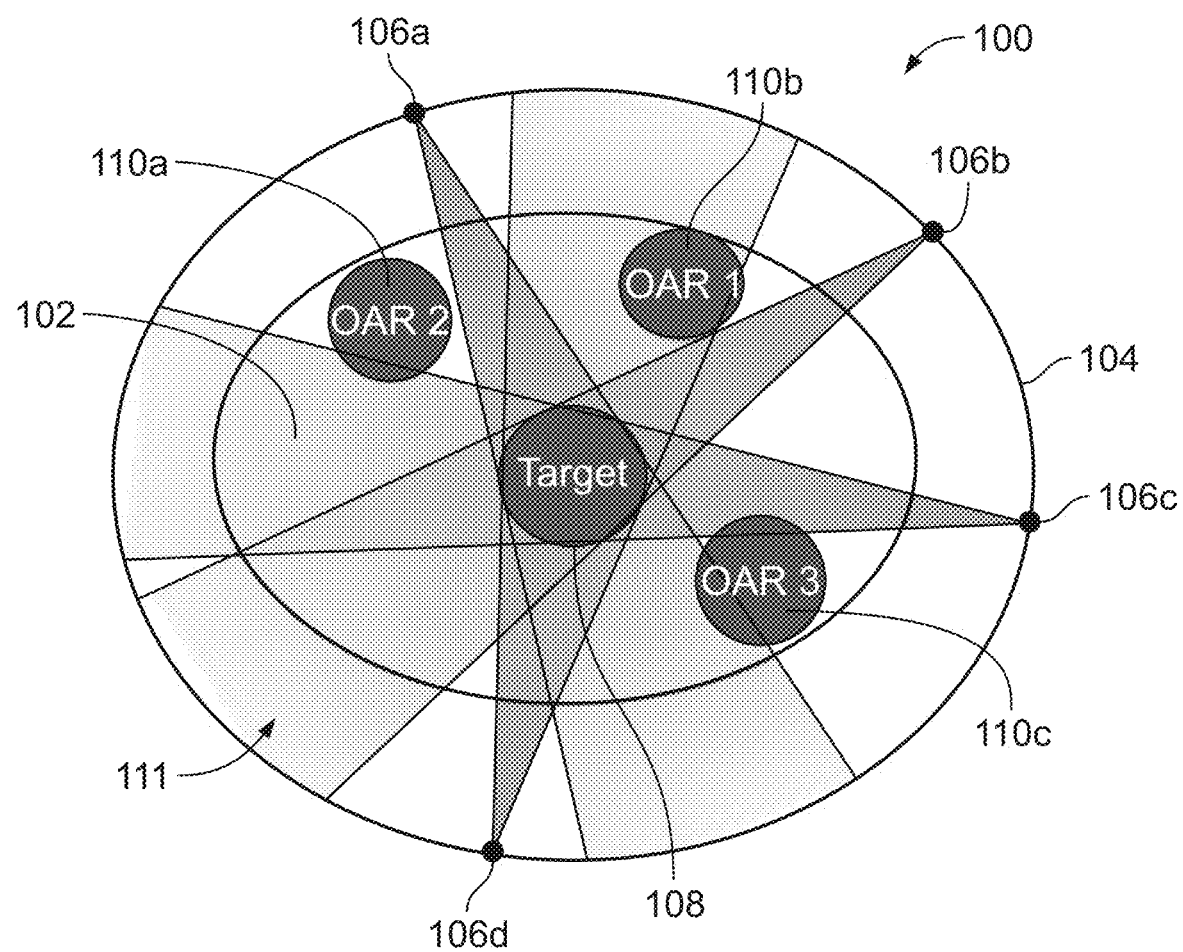
FIGS. 1A and 1B are schematic depictions of the fluence map optimization problem.

In some variations, a system configured to generate a fluence map (e.g., a treatment planning system) may be in communication with a radiation therapy system. One variation of a radiation therapy system may comprise a gantry that is movable (e.g., rotatable) about a patient treatment area, a radiation source mounted on the gantry, and a controller that is in communication with the gantry and the radiation source. Optionally, a radiation therapy system may comprise a detector located opposite the radiation source that is also in communication with the controller. The controller may provide signals to a gantry motion system to position the radiation source at a particular location with respect to the radiation treatment area and may provide a sequence of radiation beamlet data (e.g., pulse intensity, width, duration, etc.) to the radiation source based on a fluence map (e.g., a fluence map generated by any of the fluence map generation methods described herein). The radiation source may comprise a multi-leaf collimator to shape the radiation beam. A system controller may be configured to convert a fluence map into a set of gantry motion and/or multi-leaf collimator instructions (using segmentation methods, for example). A schematic depiction of a patient 102 located within the treatment area of a radiotherapy system 100 is provided in FIGS. 1A and 1B.

Figure 1B:
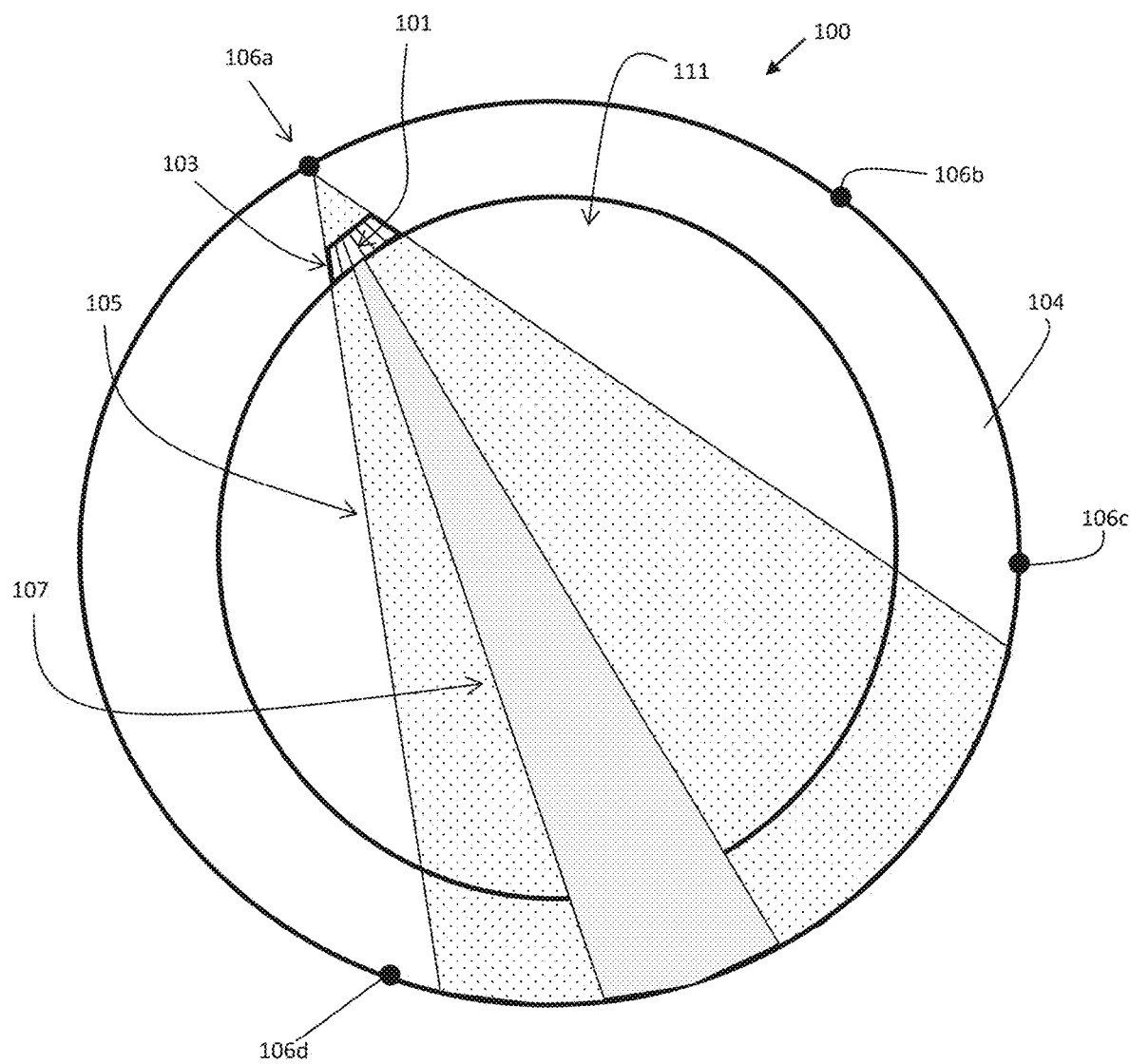

In order to solve the dose optimization problem, the radiation beam that may be delivered to a patient may be divided into beamlets. As depicted in FIG. 1B, a beamlet 107 may be a portion of a full radiation beam 105 that is defined by a multi-leaf collimator leaf 101 opening at a particular firing position (e.g., a firing position 106a with respect to a patient area 111). Given a discrete set of all possible beam angles (e.g., firing locations) around a gantry 104 (or, more generally, firing locations about a patient area), a set of all possible beamlets (a subset of which is represented by 106a, 106b, 106c, 106d) may be selected. For example, a radiation therapy system 100 having m firing positions (e.g., firing angles around a rotatable/circular gantry) may comprise a multi-leaf collimator 103 that may be positioned at each of them firing positions. The MLC may have n leaves, and as such, there may be a total of m×n possible beamlets. In some variations, a radiation therapy system comprising a binary multi-leaf collimator having 64 leaves that is located on a circular or rotatable gantry having 100 firing positions may have a total of 6400 possible beamlets. Optionally, the total number of possible beamlets may also take into account patient platform movement through the therapy system, such that a system with p patient platform positions may have a total of m×n×p possible beamlets. For example, the radiation therapy system described above may have from about 10 to about 100 patient platform positions, which may result in a number of possible beamlets from about 64,000 (64×100×10) to about 640,000 (64×100×100). Accordingly, an individual beamlet may be uniquely identified by its firing position or angle, collimator leaf index, and optionally, patient platform position. In some variations, a set of candidate beamlets for fluence map generation may be a subset of the total number of possible beamlets. For example, a set of candidate beamlets may be derived by removing the beamlets that do not intersect a volume of interest (e.g., an irradiation target volume, etc.) from the total number of possible beamlets. In some variations, the beamlets where all beamlet weights (i.e., beamlet intensities) are 0 can be omitted. A mathematical optimization problem may be solved based on the set of candidate beamlets to calculate the beamlet weights (e.g., beamlet intensities) that apply a prescribed dose of radiation to a target region/ROI 108. Fluence map optimization (FMO) is the method by which a set of "optimal" (i.e., satisfying the imposed constraints) beamlet weights are found. In some variations, a FMO or fluence map generation method may comprise computing a set of beamlet weights that deliver the prescribed dose to the target while limiting radiation dose to OARs 110a, 110b, 110c. The shading of the beamlets 106a-106d may represent the weight of that beamlet (e.g., intensity), where a darker shade represents a higher beamlet weight (i.e., greater beamlet intensity). The fluence map generated by a FMO method may result in the application of radiation according to the profile depicted in FIG. 1A, where the target 108 may receive the prescribed dose of radiation while the radiation exposure of the OARs 110a, 110b, 110c is reduced (e.g., below a selected threshold).

In some variations, volumes of interest (including irradiation target regions and irradiation-avoidance regions) may be divided into a plurality of voxels. Based on the data provided in a treatment plan, which outlines the dose distribution and profile that is prescribed for each VOI in a patient, each voxel may have an acceptable dose range. For example, a voxel in an irradiation target region may have a minimum dose threshold for the treatment session to meet treatment goals and a maximum dose threshold above which a patient may be subject to undesired radiation risk. A voxel in an irradiation-avoidance region may have a maximum dose threshold above which undesired tissue damage may be expected to occur. In some variations, this maximum dose threshold may be lower than the maximum dose threshold for the irradiation target region(s), since tissue in the irradiation-avoidance region may be particularly sensitive or prone to radiation damage. The acceptable dose range of a voxel may be calculated based on the prescribed dose for that volume of interest as specified by a treatment plan. The dose constraints on the voxels in the volumes of interest (VOIs) may be used in the fluence map generation methods described herein to derive a set of beamlet weights that meet these voxel dose constraints. In some variations, fluence map generation methods may utilize the acceptable dose range per voxel as a constraint for evaluating whether a set of beamlet weights meets clinical goals. Alternatively or additionally, fluence map generation methods may aggregate the acceptable dose ranges of all of the voxels of a volume of interest as a single-value constraint (e.g., a single-value penalty or cost function) for evaluating whether a set of beamlet weights meets clinical goals. In one variation, a fluence map generation method may comprise an iterative method including assigning a set of beamlet weights to a set of initial values (e.g., zero or a baseline value), calculating the dose per voxel based on the current value of the set of beamlet weights, comparing the calculated dose per voxel with the acceptable dose range per voxel to determine whether the current set of beamlet weights meets clinical goals and/or whether the current set of beamlet weights meets one or more stopping criteria, and if not, updating the set of beamlet weights to a new set of values. Examples of stopping criteria may include, but are not limited to, the set of beamlet weights converging to across iterations (e.g., the difference between the set of beamlet weights of the current iteration and the set of beamlet weights of a previous iteration is less than a predetermined threshold; residual r is less than less than a threshold $\epsilon$), and/or attaining an upper bound or number of iterations. Updating the set of beamlet weights from a previous iteration ($x^{k-1}$) to a new set of beamlet weights for the current iteration ($x^k$) may be based on an accelerated proximal gradient method (such as FISTA), or any proximal algorithms (such as Chambolle-Pock methods), with one or more linear penalty functions. The fluence map generation methods described herein may be used to calculate beamlet weights for delivering a dose to one or more VOIs within the acceptable dose range of each VOI. Examples of VOIs may include irradiation target regions, irradiation-avoidance regions (e.g., organs-at-risk, areas of particular radiation sensitivity), and/or any combination of such regions. Fluence mapping methods that are described in the context of generating a set of beamlet weights based on acceptable dose ranges for a single VOI may be expanded to generate a set of beamlet weights based on acceptable dose ranges for multiple VOIs.

The dose range limits of a VOI and/or a plurality of voxels in the generation of a fluence map may be represented by a penalty function. A penalty function may comprise a plurality of penalties that represent VOI or voxel criteria or conditions that a fluence map generation method seeks to fulfill. In some variations, a penalty function that may be included with a proximal gradient method (e.g., an accelerated proximal gradient method such as FISTA) for fluence map generation may be based on clinically-derived constraints or conditions and/or mathematical constraints or conditions. In some variations, a penalty function may comprise one or more linear or nonlinear (e.g., quadratic) penalties that represent constraints based on acceptable dose ranges per voxel and/or VOI (e.g., as may be extracted from a treatment plan), as well as one or more linear or nonlinear (e.g., quadratic) penalties that represent constraints based on the smoothness of a set of beamlet weights. A linear penalty may be one in which deviations from a desired set of constraints are linearly weighted when evaluating whether a solution satisfies a set of requirements, while a nonlinear penalty (e.g., a quadratic penalty) may be one in which deviations from a desired set of constraints are nonlinearly weighted by a higher-order multiplicative factor. For example, a quadratic (or $L_2$) type, penalty may amplify, or weight heavily, large deviations from a desired set of constraints (e.g., large deviations from acceptable dose ranges per voxel or VOI) when evaluating whether a solution (e.g., a set of beamlet weights) satisfies a set of requirements (e.g., dose as specified in a treatment plan). Linear (or $L_1$ type) penalties that may be included in a fluence map generation method may help converge on a set of beamlet weights that reduce the number of voxels and/or VOIs where the delivered dose exceeds the acceptable dose range. This may be described as promoting sparsity in the number of dose violations on a voxel-by-voxel or VOI-by-VOI basis. In some variations, the penalty function may be a linear penalty function (e.g., having only linear penalties) while in other variations, the penalty function may be a nonlinear penalty function (e.g., comprising one or more nonlinear penalties). Some variations of a method for generating a fluence map may comprise an accelerated proximal gradient method having a single-value penalty function, which may be derived by aggregating the dose constraints of each voxel in a volume of interest. For example, the constraints imposed by a VOI may be represented by a single-value penalty function, and an accelerated proximal gradient method may iterate on a set of beamlet weights based on the single-value penalty function of each of the VOIs in a patient. Other types of penalties that may be included in a penalty function are described in greater detail below and/or tabulated in Table 1 of FIG. 2. Any of the fluence map generation methods described herein may optionally include a step of generating one or more penalty functions (e.g., multiple single-value penalty functions that correspond to multiple VOIs, multiple penalty functions for multiple sets of voxels) that represents the clinical and/or mathematical constraints that may be relevant to a particular patient and/or set of VOIs outlined in the treatment plan. In some variations where the one or more penalty functions do not meet the smoothness criteria for fluence map generation using an accelerated proximal gradient method, a smoothing function (e.g., convex regularization, Moreau-Yosida regularization) may be applied to the one or more penalty functions.

In some variations, convex optimization techniques may be used to address fluence map generation problems that may arise during radiation planning. For example, proximal algorithms may be used for solving very large scale, constrained convex optimization problems with nondifferentiable objective functions. Some variations may comprise the use of proximal algorithms to address fluence map generation issues during treatment planning. In some variations, a method for fluence map generation may comprise the use of the Alternating Direction Method of Multipliers (ADMM), while in other variations, a method for fluence map generation may comprise the use of a proximal algorithm such as the Chambolle-Pock method. The Chambolle-Pock method may be able to handle nonquadratic dose-penalty terms, including nondifferentiable $L_1$-based penalties in the objective, and also hard constraints on the amount of radiation delivered to the planning target volume (PTV) and OARs. Another class of algorithms, accelerated proximal gradient methods (including FISTA, for example) may also be used in a fluence map generation method. These accelerated methods have a convergence rate which has been shown to be in some sense optimal for first-order methods.

Disclosed herein are methods for generating a fluence map comprising a set of beamlet intensities that delivers radiation dose to every VOI within the acceptable dose range for that VOI. For example, these methods may generate a fluence map such that the prescribed radiation dose to irradiation target regions (e.g., planning target volumes PTV, tumor regions, etc.) while not exceeding a maximum dose to irradiation-avoidance regions (e.g., organs at risk OARs).

The acceptable radiation dose range for a VOI (and/or for the individual voxels within the VOI) may be determined at least in part by a treatment plan. In some variations, a treatment plan may be generated based on images of the patient that have been acquired before a treatment session (e.g., during a diagnostic imaging session) and/or during a previous treatment session or fraction.

Some variations for generating a fluence map may comprise generating a set of beamlet weights or intensities using an accelerated proximal gradient method, such as FISTA or a proximal method, such as the Chambolle-Pock method. FISTA has been used for solving inverse problems in signal or image processing and in particular, for compression, denoising, image restoration, sparse approximation of signals, compressed sensing and the like. Accelerated proximal gradient methods may include a penalty function having a linear or $L_1$ penalty term to promote signal sparsity so that signals can be compressed. Since signal sparsity, and/or data compression, and/or image reconstruction are not primary goals of fluence map optimization, accelerated proximal gradient methods such as FISTA and proximal methods such as Chambolle-Pock have not been considered for generating a set of beamlet weights or intensities for radiation treatment plans and systems. However, as described herein, accelerated proximal gradient methods such as FISTA may be able to provide a computationally efficient method to generate a fluence map. The fluence map generation methods described herein may comprise using an accelerated proximal gradient method such as FISTA with one or more linear or $L_1$ penalty terms. In some variations, the $L_1$ penalty terms may be smoothed by a regularization method to help reduce discontinuities in the FISTA method. FISTA with linear penalty functions having one or more $L_1$ penalty terms may be readily implemented on multi-core processors (CPUs and/or GPUs), facilitate faster convergence to a final set of beamlet weights, and/or may promote better plan conformance to user or clinician-specified planning goals or treatment plans. For example, FISTA with $L_1$ penalty terms may result in a set of beamlet weights that deliver dose to VOIs that conform better to treatment plan specifications as compared to accelerated proximal gradient methods have $L_2$ penalty terms. Fluence map generation methods that have $L_2$ penalty terms may result in a set of beamlet weights that deliver fluence such that a higher proportion of VOIs or voxels receive dose levels that are outside of their acceptable dose ranges (as compared to methods with $L_1$ penalty terms). Fluence map generation methods with $L_2$ penalties may require users or clinicians to over-constrain the problem or iteratively tuning the objective weights, etc., resulting in higher computational load on the processor and a fluence map that does not conform as closely to treatment plan specifications.

Figure 1C:
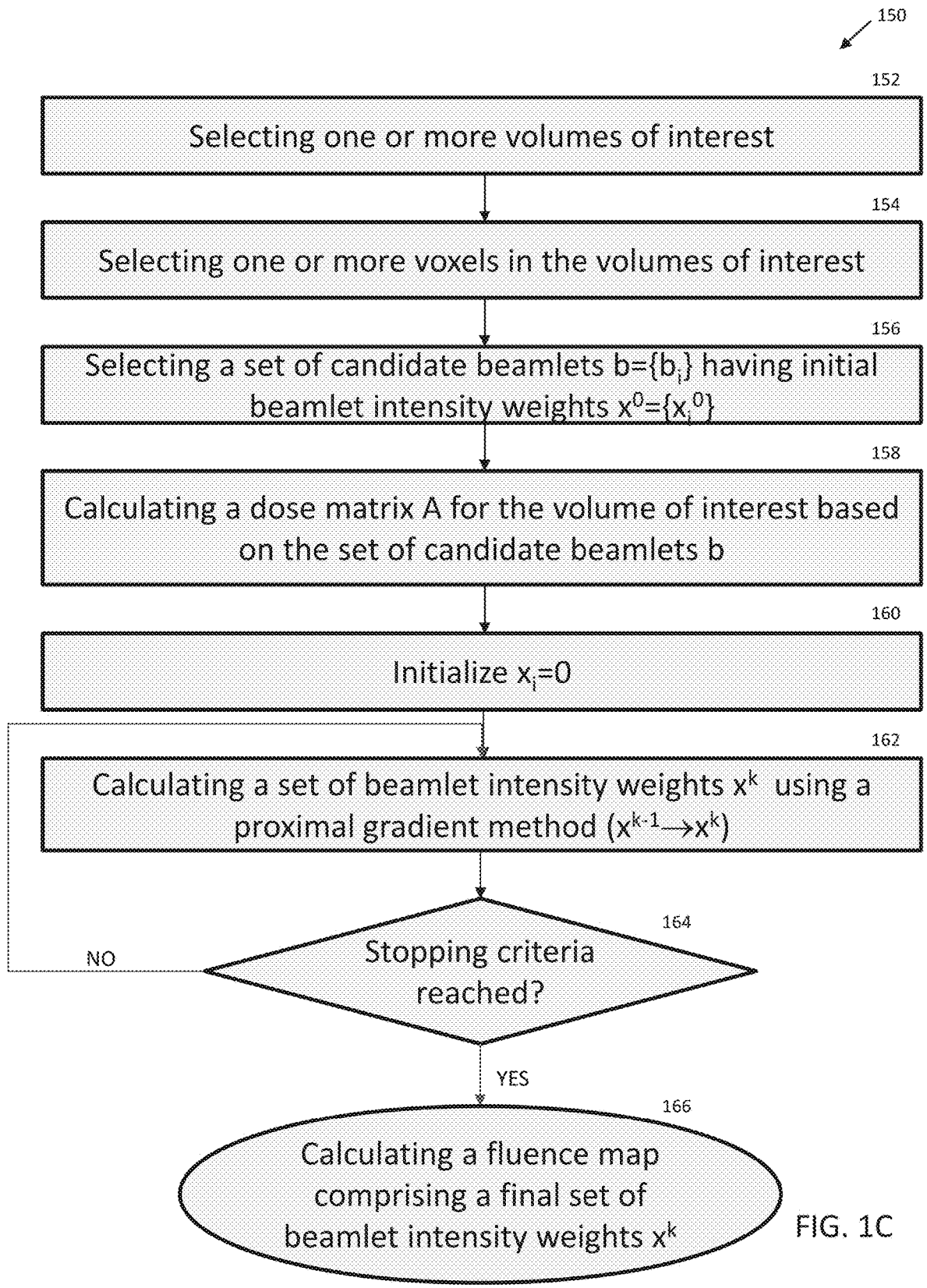
FIG. 1C depicts one variation of a method for generating a fluence map.

FIG. 1C depicts one variation of a method for generating a fluence map. The method 150 may comprise selecting 152 one or more volumes of interest (VOIs). A VOI may include one or more irradiation target (e.g., PTV, tumor region, etc.) and/or may include one or more irradiation-avoidance regions). The method 150 may comprise selecting 154 voxels in the one or more VOIs. In some variations, the selected voxels may, cumulatively, approximate the overall size, shape and location of each of the VOIs. The method 150 may comprise selecting 156 a set of candidate beamlets $b=\{b_i\}$ having initial beamlet intensity weights $x^0=\{x_i^0\}$. The method 150 may comprise calculating 158 a dose matrix A for each volume of interest based on the set of candidate beamlets b. The dose matrix A may represent per-voxel dose delivered to each of the plurality of voxels by the set of candidate beamlets b. In some variations, the method may comprise initializing 160 beamlet intensity weights to zero (e.g., the initial set of beamlet weights $x^0$ may be an all-zero vector). Next, the method may comprise calculating 162 a set of beamlet intensity weights $x^k$ by adjusting the initial beamlet intensity weights according to a proximal gradient method update ($x^{k-1} \rightarrow x^k$) with a penalty function containing one or more linear penalties, such as an accelerated proximal gradient method. This may be an iterative method where a set of beamlet intensity weights is adjusted based on the penalty function until one or more stopping criteria are met (step 164), and may be any of the methods described below. For example, the accelerated proximal gradient method may be a FISTA method having one or more $L_1$ cost or penalty functions (e.g., as explained further below and represented in FIGS. 7-8). In some variations, calculating 162 a set of beamlet intensity weights may comprise adjusting beamlet intensity weights according to a proximal gradient method or more generally, a proximal method. In some variations, the stopping criteria may include convergence of the set of beamlet intensity weights to a set of intensity values. Convergence from one iteration to the next may be determined, for example, by comparing the set of beamlet intensity weights of iteration x to the set from iteration x−1 and taking the difference (e.g., a residual) in values between the two sets. If the difference is smaller than a predetermined threshold the stopping criterion may be met and the iteration may stop. Other stopping criteria are described below. Alternatively or additionally, iteration may stop if the number of iterations attains an upper bound. After meeting the stopping criteria, the method 150 may comprise calculating a fluence map comprising a final set of beamlet intensity weights $x^k$.

Additional details regarding these steps, including illustrative examples, are provided below.

Figure 1D:
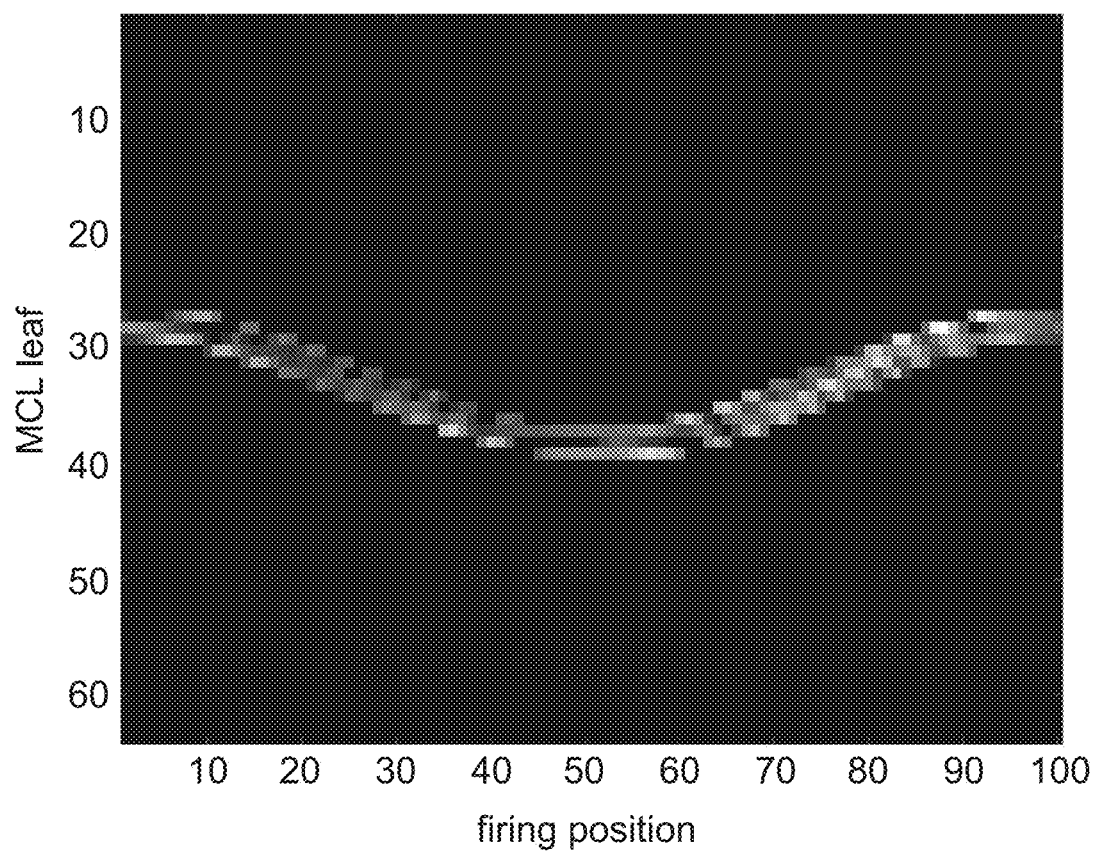
FIG. 1D depicts one example of a fluence map and FIG. 1E depicts an axial slice of simulated dose delivered to a patient based on the fluence map of FIG. 1D.
Figure 1E:
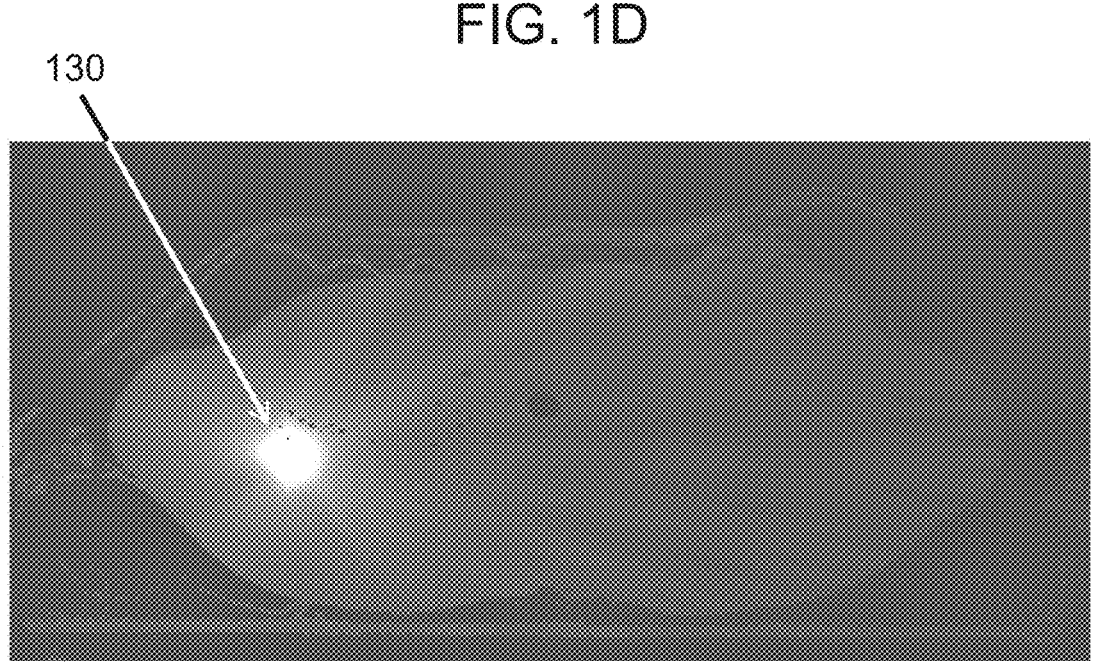

FIG. 1D depicts one example of a fluence map (i.e., set of beamlet intensities) that has been generated using the FISTA method having a smoothed $L_1$ penalty function. This fluence map was generated for a radiation therapy system having 100 firing positions (e.g., 100 firing angles around a circular gantry) and a multi-leaf collimator having 60 leaves. In this example, the multi-leaf collimator is a binary multi-leaf collimator. The fluence map in FIG. 1D may represent the beamlet intensity for a single patient platform position, e.g., a single tomographic slice. The intensity of a pixel in the plot may be proportional to the beamlet intensity. As the gantry moves the radiation source from firing position 1 to firing position 100, the multi-leaf collimator opens certain leaves at each of those firing locations. The intensity of the radiation beam at a particular firing position for a particular leaf is represented by the intensity of the pixel in the fluence map (where a black pixel represents a beamlet intensity of zero and a white pixel represents a beamlet having the maximum allowable intensity). FIG. 1E depicts an axial slice of a simulated patient body where radiation beamlets were delivered based on the fluence map of FIG. 1D. The fluence map of FIG. 1D resulted in a dose delivery that concentrates on a ROI 130, with little or no irradiation of other patient regions.

One of the computational challenges of fluence map optimization is working with the dose calculation matrix, a huge matrix which (despite its sparsity) has a very large number of nonzero entries. When applied to fluence map optimization, the Alternating Direction Method of Multipliers requires solving a linear system of equations involving this dose calculation matrix at each iteration. This is a significant and potentially prohibitive computational expense. While decomposition methods are available to reduce this computational burden, such methods may lead to a more complicated algorithm that is more difficult to implement, and takes more iterations to converge, as compared with a straightforward implementation of ADMM (which might be unworkable due to the size of the dose calculation matrix). The Chambolle-Pock algorithm and accelerated proximal gradient methods (e.g., FISTA), on the other hand, may be advantageous in that they perform matrix-vector multiplications with the dose calculation matrix at each iteration. These methods may not include solving a linear system at each iteration, and hence may not include decomposition methods to make such a calculation manageable. The fluence map generation methods described herein may be effective algorithms that parallelize naturally and are particularly easy to implement in a controller of a radiotherapy system.

The general fluence map optimization problem contemplated in this document is:

$$\operatorname*{minimize}_{x} \Gamma(A_0 x) + \sum_{i=0}^{N} \Phi_i(A_i x) + \Psi(Dx) + \Theta(x), \quad (1)$$

where the matrices $A_i$ are the dose-calculation matrices for one or more VOIs (e.g., planning target volume PTV, irradiation target regions or volumes, OARs, irradiation avoidance regions or volumes, the tumor, etc.), N is the number of OARs, the matrix D represents a discrete derivative or gradient operator, and the functions $\Gamma$, $\Phi_i$, $\Psi$ and $\Theta$, are convex penalty functions. The term $\Gamma(A_0 x)$ encourages or defines a minimum level of radiation to be delivered to the PTV, while the terms $(A_i x)$ encourage or require the radiation delivered to the PTV and OARs not to exceed a maximum dosage. The regularization terms $\Psi(Dx)$ and $\Theta(x)$ encourage smooth or piecewise-smooth nonnegative fluence maps. Problem (1) may contain most standard fluence map optimization formulations as special cases, with simple and convenient choices of the convex penalty functions.

The optimization algorithms described herein may be able to handle nonquadratic and nondifferentiable penalty terms $\Gamma$, $\Phi_i$ and $\Psi$ in fluence map optimization. By taking the penalty functions to be indicator functions (defined in equation (4)), hard constraints may be enforced on the amount of radiation delivered to the PTV and OARs. The advantages of the $L_1$-norm may apply in fluence map optimization, as will be described further below.

Disclosed herein are fluence map generation methods that comprise proximal algorithms with one or more penalties, such as $L_1$ penalties. In one variation, the Chambolle-Pock algorithm may be used to solve problem (1) in the case where the penalty functions $\Gamma$, $\Phi_i$, $\Psi$ and $\Theta$ have proximal operators that may be evaluated efficiently. This may include most fluence map optimization problems encountered in practice, including those with hard constraints and nondifferentiable objective functions. In some variations, a fluence map generation method may comprise a smoothing technique from convex analysis, such as the Moreau-Yosida regularization, to smooth out the penalty functions $\Gamma$, $\Phi_i$ and $\Psi$, and an accelerated proximal gradient method (such as FISTA) to solve the smoothed out problem (which may involve nonquadratic penalties). The smoothed problem may contain, as a special case, all fluence map generation problems considered in the unified approach to inversion problems in intensity modulated radiation therapy (IMRT).

Fluence map generation methods may include the selection of penalty functions $\Gamma$, $\Phi_i$, $\Psi$ and $\Theta$. The problem defined in equation (1) may contain most standard FMO models as special cases, with simple and convenient choices of the penalty functions. Examples of penalty functions that may be used in the fluence map generation methods described herein are summarized in table 1, depicted in FIG. 2.

Often $\Gamma$ is taken to be a one-sided quadratic penalty $$\Gamma(v) = \|(v-l)_-\|_2^2,$$

where l is a vector that lists the prescribed doses that are to be delivered to each voxel in the tumor, but an arguably superior option is to take $\Gamma$ to be a one-sided L1-norm-based penalty:

$$\Gamma(v) = \|(v-l)_-\|_1.$$

The usual benefits of $L_1$-norm, such as robustness against outliers, apply in this context as well. By taking $\Gamma$ to be a one-sided $L_1$-based penalty, a small number of voxels in the tumor are allowed to be significantly underdosed. This extra flexibility can allow for a reduction in the amount of radiation delivered to OARs, leading to an overall superior treatment plan. An $L_2$-based penalty does not allow this flexibility—any significant underdosing is penalized severely. Additionally, an $L_2$-based penalty tends to allow a large number of voxels to be slightly underdosed, which is undesirable, and on practical FMO problems, consistently leads to slight underdosing of the target, and slight overdosing of the OAR. In comparison, an $L_1$-based penalty is discourages the presence of small residuals, and encourages most residuals to be 0. A third important option is to take $\Gamma$ to be an indicator function:

$$\Gamma(v) = I_{\geq \ell}(v) = \begin{cases} 0 & \text{if } v \geq \ell \\ \infty & \text{otherwise} \end{cases} \quad (2)$$

With this choice of $\Gamma$, the hard constraint that $(A_0 x) \geq l$ may be applied or enforced to the fluence map generation method.

Similar considerations apply to the penalty functions $\Phi_i$, which are chosen to encourage or enforce upper bounds on the dose delivered to the tumor and to the OARs. In some variations, $\Phi_i$ may include a one-sided $L_1$-based penalty $\Phi_i(y_i) = \alpha_i \|y_i - u_i\|_1$ a one-sided $L_2$-based penalty $\Phi_i(y_i) = (\alpha_i/2)\|y_i - u_i\|_2^2$, or an indicator function penalty $$\Phi_i(y_i) = I_{\geq u_i}(y_i) = \begin{cases} 0 & \text{if } y_i \geq u_i \\ \infty & \text{otherwise} \end{cases}$$

This indicator function penalty may be able to enforce the hard constraint that $A_i x \leq u_i$. In some variations, the method may include the penalty function $$\Phi_i(y_i) = \alpha_i \|(y_i - u_i)_+\|_1 + \frac{\beta_i}{2}\|y_i\|_2^2. \quad (3)$$

By selecting $\Phi_i$ as indicated above, $$\Phi_i(A_i x) = \alpha_i \|(A_i x - u_i)_+\|_1 + \frac{\beta_i}{2}\|A_i x\|_2^2.$$

The term $\beta_i/2\|A_ix\|_2^2$ may be thought of as providing additional guidance on how to select x, in cases where Aix<ui is easily satisfied. (We take $\beta_0=0$, because there is no need for an additional penalty for radiation delivered to the tumor.)

Some variations of fluence map optimization methods and/or fluence map generation methods may include a quadratic regularization term $$\Psi(Dx) = \frac{1}{2}\|Dx\|_2^2 = \sum_{m=1}^{M} \frac{1}{2}\|D_x x_m\|_2^2$$

where M is the number of beamlets in the IMRT system, x is the vector of beamlet intensities, $x_m$ is the mth block of x (consisting of beamlet intensities for the mth beamlet), and each matrix $D_m$ represents a discrete derivative or gradient operator. This regularization term encourages adjacent beamlets to have similar intensities, thereby leading to less chaotic fluence maps. The regularization term may facilitate (i.e., speed up) convergence of optimization algorithms so that a solution (e.g., a set of beamlet weights or intensities) may be attained in fewer iterations. However, due to the use of a quadratic penalty function, large components of Dx may be penalized severely (because they get squared), and as a result this regularization term tends not to allow any sharp jumps in intensity between adjacent beamlets. This may detract from the creation of treatment plans that are highly conformable to the tumor. A similar problem may be encountered in image restoration and reconstruction problems, where the use of a quadratic regularization term does not allow sharp edges in the image to be preserved. One example of a regularization term may be the total variation regularization term $$\Psi(Dx) = \|Dx\|_1 = \sum_{m=1}^{M} \|D_m x_m\|_1.$$

Alternatively, $\Psi$ may be the indicator function for an $L_\infty$-norm ball. A hard upper bound on the change in intensity between adjacent beamlets may be enforced. These choices of $\Psi$ may facilitate computations that are able to handle nonquadratic and nondifferentiable penalty terms.

Typically $\Theta$ is chosen to be the indicator function for the nonnegative orthant, denoted by $I_{\geq 0}$. In this case, the term $\Theta(x)$ in the objective simply enforces the constraint that $x \geq 0$. $\Theta$ may also be chosen to enforce upper bounds on the beamlet intensities; for example, $\Theta$ may be the indicator function of the set $S=\{x|a \leq x \leq b\}$, for given vectors a and b. Other choices of $\Theta$ are possible, such as $\Theta(x)=I_{\geq o}(x)+(\epsilon/2)\|x\|_2^2$ or $\Theta(x)=I_{\geq o}(x)+\epsilon\|x\|_1$. These choices of $\Theta$ control the size of x while also enforcing $x \geq 0$. Penalizing the $L_1$-norm of x could be useful, for example, to limit the number of beamlets that fire during treatment delivery (in other words, to promote sparsity in the fluence map). Penalizing the $L_2$-norm of x may help to limit the total energy delivered during treatment.

In some variations, problem (1) may be solved using the Chambolle-Pock algorithm, under the assumption that the penalty functions $\Gamma$, $\Phi_i$, $\Psi$ and $\Theta$ have proximal operators that can be evaluated efficiently. This may include one or more (e.g., all) of the penalty functions described herein. Also disclosed are numerical results for the FMO problem $$\underset{x}{\text{minimize}}\, \mu\|(A_0 x - \ell)_-\|_1 + \sum_{i=0}^{N} \alpha_i \|(A_i x - u_i)_i\|_1 + \sum_{i=1}^{N} \frac{\beta_i}{2}\|A_i x\|_2^2 + \eta\|Dx\|_1$$

subject to $x \geq 0$.

This is the special case of problem (1) where $\Phi_i$ is given by equation (3) and $\Gamma(v)=u\|(v-1)_-\|_1$, $\Psi(Y_{N+1})=\eta\|Y_{N+1}\|_1$, and $\Theta=I_{\geq 0}$. Also disclosed are numerical results for the FMO problem $$\underset{x}{\text{minimize}} \sum_{i=1}^{N} \frac{\beta_i}{2}\|A_i x\|_2^2 + \eta\|Dx\|_1$$

subject to $A_0 x \geq \ell$ $x \geq 0$.

This is the special case of problem (1) where $\Gamma$ is taken to be the indicator function given by equation (2), $\Phi_i(y_i)=(\beta_i/2)\|y_i\|_2^2$ for $1, \ldots, N$, $\Phi_0=0$, $\Psi(y_{N+1})=\eta\|y_{N+1}\|_1$, and $\Theta=I_{\geq 0}$ Table 2 summarizes the notation and definitions used herein.

In convex analysis, a function $f: \mathbb{R}^n \to \mathbb{R} \cup \{\infty\}$ is called "closed" when it is lower semicontinuous. This is a mild condition satisfied by most convex functions that one encounters in practice. A function $f: \mathbb{R}^n \to \mathbb{R} \cup \{\infty\}$ is called "proper" when $f(x) < \infty$ for at least one point $x \in \mathbb{R}^n$.

Indicator and Projection Functions.

Let $C \subset \mathbb{R}^n$ be a closed convex set. The indicator function of C is the convex function $I_C: \mathbb{R}^n \to \mathbb{R} \cup \{\infty\}$ defined by $$I_C(x) = \begin{cases} 0 & \text{if } x \in C, \\ \infty & \text{otherwise.} \end{cases} \quad (4)$$

Indicator functions are useful in convex optimization (including any of the methods described herein) for enforcing hard constraints on the optimization variable x. The problem of minimizing $f(x)$ subject to the constraint that $x \in C$, is equivalent to the problem of minimizing $f(x)+I_C(x)$. Indicator functions are highly nondifferentiable, but this poses no problem for proximal algorithms, which are able to handle indicator functions naturally.

When $C=[a, b]^m=[a, b] \times \ldots \times [a, b]=\{x \in \mathbb{R}^n | a \leq x_j \leq b$ for $j=1, \ldots, m\}$, the indicator function of C is denoted by $I_{[a,b]}$ rather than by $I_{[a,b]^m}$. The notation $I_{\geq l}$, where $l \in \mathbb{R}^n$, denotes the indicator function of the set $S=\{x \in \mathbb{R}^n | x \geq l\}$, where the inequality $x \geq l$ is interpreted to mean that $x_j \geq l_j$ for $j=1, \ldots, m$.

The function that projects onto C is denoted by $P_C$:

$$P_C(x) = \text{closest point to } x \text{ in } C = \underset{u \in C}{\text{argmin}}\|u - x\|_2.$$

When $C=[a, b]^m$, the function that projects onto C will be denoted by $P_{[a,b]}$ rather than by $P_{[a,b]^m}$. The notation $P_{\geq l}$ to denotes the function that projects onto the set $S=\{x \in \mathbb{R}^n | x \geq l\}$. Note that $P_{\geq l}(x)=\max(x, 1)$ (where the maximum is taken componentwise).

Conjugate.

The convex conjugate of a function $f: \mathbb{R}^n \to \mathbb{R} \cup \{\infty\}$ is the function $f^*: \mathbb{R}^n \to \mathbb{R} \cup \{\infty\}$ defined by $$f^*(z) = \sup_{x \in S^n} \langle z, x \rangle - f(x).$$

The convex conjugate $f^*$ is a "dual version" of f which tends to appear when formulating dual problems in convex optimization. When $f$ is closed and convex, $f$ can be recovered from $f^*$ via the formula $f = f^{**}$.

The following "separable sum" rule for conjugates will be useful later. Suppose $f$ is a block-separable sum:

$$f(x_1, \ldots, x_K) = \sum_{k=1}^{K} f_k(x_k). \tag{5}$$

Then $f^*(z_1, \ldots, z_K) = \sum_{k=1}^{K} f^*_k(z_k)$. The input vectors $x_1, \ldots, x_K$ can be viewed as blocks of a larger vector x, and the vectors $z_1, \ldots, z_K$ can be viewed as blocks of a larger vector z.

Proximal Operator.

Let $f: \mathbb{R}^n \to \mathbb{R} \cup \{\infty\}$ be a proper closed convex function. The proximal operator (also known as "prox-operator") of $f$, with parameter t>0, is defined by $$\text{prox}_{tf}(x) = \operatorname*{argmin}_{u} f(u) + \frac{1}{2t}\|u - x\|_2^2. \tag{6}$$

Proximal algorithms are iterative algorithms that require the evaluation of various prox-operators at each iteration. For many important convex penalty functions, the prox-operator has a simple closed-form expression and can be evaluated very efficiently, at a computational cost that is linear in m. The term "proximable" may describe a function whose prox-operator can be evaluated efficiently.

Several useful rules for evaluating prox-operators are listed in table 3, depicted in FIG. 4. In this table, the functions $f$ and $f_k$ are assumed to be proper closed convex. Formula 3.3 is known as the Moreau decomposition and is very useful for proximal algorithms because it expresses the prox-operator of $f^*$ in terms of the prox-operator of $f$. If the prox-operator off can be evaluated efficiently, then the prox-operator of $f^*$ can be evaluated equally efficiently. (The term "decomposition" suggests that x has been decomposed as a sum of prox-operator terms.) In formula 3.1, the function g is a separable sum of the functions $f_k$. The input vectors $x_1, \ldots, x_K$ can be viewed as blocks of a larger vector x. According to this rule, evaluating the prox-operator of the separable sum g reduces to independently evaluating the prox-operators of the functions $f_k$. Rule 3.4 can be derived by using the Moreau decomposition to express the prox-operator of $f(x)=\|x_+\|_1$ in terms of the prox-operator of its conjugate $f^*(z)=I_{[0,1]}(z)$. In the last two rows of the table, $p_j$ denotes the jth component of the vector $\text{prox}_{tg}(x)$, and $x_j$ denotes the jth component of x.

One of the most fundamental proximal algorithms, the proximal gradient method solves optimization problems of the form $$\text{minimize } f(x)+g(x) \tag{7}$$

where $f$ and g are closed convex functions and $f$ is differentiable with a Lipschitz continuous gradient. The proximal gradient iteration for a fixed step size t>0 is recorded in algorithm 1 (FIG. 5). If t≤2/L, where L is the Lipschitz constant for $\nabla f$, then the proximal gradient iteration is guaranteed to converge to a minimizer of (7), assuming that a minimizer exists.

In the special case where $g(x)=I_C(x)$, where C is a closed convex set and $I_C$ is the indicator function of C, problem (7) is equivalent to $$\text{minimize } f(x)$$

$$\text{subject to } x \in C. \tag{8}$$

The proximal gradient iteration reduces to $$x_k = P_C(x_{k-1} - t\nabla f(x_{k-1})),$$

where $P_C$ is the function that projects onto C. In this case, the proximal gradient method is known as the projected gradient method.

While a proximal gradient method may be used with a fixed step size, a significant advantage of the proximal gradient method is that there is a simple and effective line search procedure that may be used to select the step size adaptively at each iteration. One variation of a proximal gradient method with line search is represented in algorithm 2 (FIG. 6).

One variation of a fluence map generation method may comprise accelerated versions of the projected gradient method and the proximal gradient method for radiation treatment planning. For example, FISTA (short for "fast iterative shrinkage-thresholding algorithm"). FISTA is an accelerated version of the proximal gradient method for solving problem (7), where (as before) $f$ and g are closed convex functions, and $f$ is differentiable with a Lipschitz continuous gradient (with Lipschitz constant L>0). One variation of a FISTA iteration for a fixed step size t>0 is represented in algorithm 3 (FIG. 7). When t=1/L, this iteration converges at a rate of $1/k^2$, whereas the proximal gradient iteration only converges at a rate of 1/k. FISTA's convergence rate of $1/k^2$ is may be desirable or optimal for a first-order method.

The Chambolle-Pock algorithm solves optimization problems of the canonical form $$\text{minimize } f(x)+g(Ax) \tag{9}$$

where $f: \mathbb{R}^n \to \mathbb{R}$ and g: $\mathbb{R}^n \to \mathbb{R}$ are proper closed convex functions and $A \in \mathbb{R}^{m \times n}$ is a matrix. This canonical problem form may be useful because many important problems in areas such as signal and image processing can be expressed in the form (9) with particularly simple choices of $f$, g, and A. By "simple", we mean specifically that the prox-operators of $f$ and g can be evaluated inexpensively, and that multiplications by A and by AT can be performed efficiently. The fluence map optimization problems considered herein may be conveniently expressed in this form. (The problem form (9) may be addressed by the Fenchel-Rockafellar approach to duality, which takes this problem form as a starting point.)

The Chambolle-Pock algorithm is a primal-dual algorithm, meaning that it simultaneously solves the primal problem (9) and the dual problem, which is $$\operatorname*{minimize}_{z} f^*(-A^T z) + g^*(z).$$

One variation of a Chambolle-Pock iteration with step sizes s and t, and overrelaxation parameter $\rho \in (0, 2)$, is represented in algorithm 5 (FIG. 9). At each iteration we perform matrix-vector multiplications by A and $A^T$ are performed, but are not required to solve linear systems involving A. This is an advantage of the Chambolle-Pock algorithm over Douglas-Rachford-based methods such as ADMM. Algorithm 5 (FIG. 9) is an overrelaxed version of the Chambolle-Pock algorithm. The step sizes s and t are required to satisfy $st\|A\|^2 \leq 1$, where $\|\cdot\|$ is the matrix norm induced by the $L_2$-norm. When this step size restriction is satisfied, the algorithm 5 may be expected to converge to a minimizer for the problem (9) (assuming that a minimizer exists). While one choice of s and t is $s=t=1/\|A\|$, convergence may be improved substantially by tuning the values of s and t.

While the Chambolle-Pock algorithm may facilitate the generation of a solution for fluence map optimization problems, one might hope to achieve faster convergence by using accelerated methods such as FISTA which have an optimal (among first-order methods) convergence rate of $O(1/k^2)$ (where k is the iteration number). When accelerated methods can be applied, this $O(1/k^2)$ convergence rate can be significantly faster than the $O(1/k)$ convergence rate of the Chambolle-Pock algorithm. Another advantage of FISTA is that simple and effective line search procedures are available, meaning that there is no difficulty with step size selection. Thus, the use of accelerated proximal gradient methods (specifically, FISTA) may be preferred for fluence map optimization.

The difficulty in using the proximal gradient method for fluence map optimization is that one must first express the optimization problem in the form (7), with a differentiable function $f$ and a simple (i.e., proximable) function g, and this is not always possible. This challenge may be addressed by smoothing out the nondifferentiable penalty functions appearing in problem (1). Convex analysis provides an elegant way to smooth out a nondifferentiable convex function—the Moreau-Yosida regularization.

Moreau-Yosida Regularization.

Let $\phi: \mathbb{R}^n \to \mathbb{R} \cup \{\infty\}$ be closed and convex. The Moreau-Yosida regularization of $\phi$ with parameter $\gamma > 0$ is defined by $$\phi^{(\gamma)}(x) = \inf_{u \in R^n} \phi(u) + \frac{1}{2t}\|u - x\|_2^2. \quad (11)$$

It can be shown that $\phi^{(\gamma)}: \mathbb{R}^n \to \mathbb{R}$ is a convex, differentiable approximation to $\phi$, and that the gradient of $\phi^\gamma$ is given by the formula $$\nabla \phi^{(\gamma)}(x) = \frac{1}{t}(x - prox_{\gamma\phi}(x)). \quad (12)$$

Figure 12:
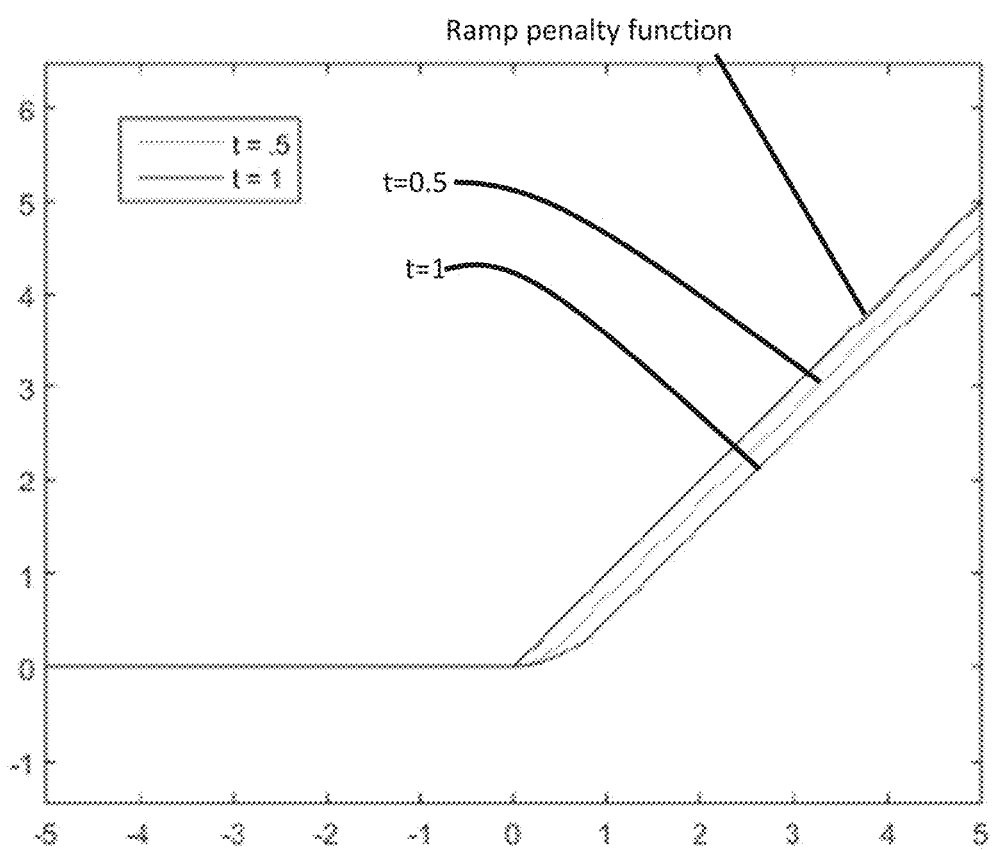
FIG. 12 depicts the Moreau-Yosida regularizations of the ramp penalty function with parameters t=1 and t=0.5.

The gradient of $\phi^{(\gamma)}$ is Lipschitz continuous with Lipschitz constant $L = 1/t$. The parameter $\gamma$ controls the amount of smoothing—for small values of $\gamma$, there is little smoothing and $\phi^{(\gamma)}$ is a close approximation to $\phi$. Correspondingly, when $\gamma$ is small, the Lipschitz constant L is large. FIG. 12 shows the Moreau-Yosida regularizations of the ramp penalty function with parameters $t=1$ and $t=0.5$. Note that the Moreau-Yosida regularizations are differentiable, whereas the ramp penalty function is not.

Note that $$\phi^{(\gamma)}(x) = \phi(prox_{\gamma\phi}(x)) + \frac{1}{2\gamma}\|prox_{t\phi}(x) - x\|_2^2.$$

When $\phi = I_C$, the indicator function of a closed convex set C, we have $$\phi^{(\gamma)}(x) = \frac{1}{2\gamma}\|P_C(x) - x\|_2^2. \quad (13)$$

This is the proximity function that is used as the basis for the unified approach to inversion problems in IMRT presented in. The gradient of the proximity function follows from equation (12): $\nabla \phi^{(\gamma)}(x) = (1/\gamma)(x - P_C(x))$.

Smoothed FMO Problem.

Below, the problem (1) is replaced with the smoothed problem $$\operatorname*{minimize}_{x} \Gamma^{(\gamma)}(A_0 x) + \sum_{i=0}^{N} \Phi_{(i)}^{(\gamma)}(A_i x) + \Psi^{(\gamma)}(Dx) + \Theta(x). \quad (14)$$

The functions $\Gamma^{(\gamma)}$, $\Phi_i^{(\gamma)}$, and $\Psi^{(\gamma)}$ are the Moreau-Yosida regularizations (with parameter $\gamma > 0$ of the functions $\Gamma$, $\Phi_i$, and $\Psi$ from problem (1). The function $\Theta$ may not be smoothed. In some variations, the same smoothing parameter $\gamma$ may be used for each penalty function, but other smoothing parameters may also be used. It is assumed that the (possibly nondifferentiable) functions $\Gamma$, $\Phi_i$, $\Psi$ and $\Theta$ have prox-operators that can be evaluated efficiently.

As a special case, when $\Gamma$, $\Phi_i$, and $\Psi$ are taken to be indicator functions, their Moreau-Yosida regularizations are proximity functions (defined in equation (13)) and may be used with the fluence map optimization problem considered in the unified approach to inversion problems in IMRT. The smoothed problem may be solved using the projected gradient method, rather than an accelerated projected gradient method.

The smoothed problem as indicated in equation (14) may be solved using accelerated proximal gradient methods. Problem (14) has the form (7), where $$f(x) = \Gamma^{(\gamma)}(A_0 x) + \sum_{i=0}^{N} \Phi_i^{(\gamma)}(A_i x) + \Psi^{(\gamma)}(Dx) \quad (15)$$

and $g = \Theta$. When using accelerated proximal gradient methods, each iteration may comprise computing the gradient of $f$ and the prox-operator of g. The prox-operator of $g = \Theta$ may be computed efficiently by assumption. Hence, it remains only to show how the gradient of $f$ can be computed efficiently.

By the chain rule, the gradient of $f$ is given by $$\nabla f(x) = A_0^T \nabla \Gamma^{(\gamma)}(A_0 x) + \sum_{i=0}^{N} A_i^T \nabla \Phi_i^{(\gamma)}(A_i x) + D^T \nabla \Psi^{(\gamma)}(Dx).$$

The gradients on the right can be computed using equation (12):

$$\nabla \Gamma^{(\gamma)}(v) = \frac{1}{\gamma}(v - prox_{\gamma\Gamma}(v)),$$

$$\nabla \Phi_i^{(\gamma)}(y_i) = \frac{1}{\gamma}(y_i - prox_{\gamma\Phi_i}(y_i)),$$

$$\nabla \Psi^{(\gamma)}(y_{N+1}) = \frac{1}{\gamma}(y_{N+1} - prox_{\gamma\Phi}(y_{N+1})).$$

Each of these gradients can be computed efficiently because we are assuming that the prox-operators of $\Gamma$, $\Phi_i$, and $\Psi$ are inexpensive.

When using the proximal gradient method or FISTA with a fixed step size to solve problem (7), the step size is typically chosen to be t=1/L, where L is the Lipschitz constant for $\nabla f$. In practice, the Lipschitz constant for $\nabla f$ is usually not known exactly, so L is taken to be the best available upper bound for the Lipschitz constant for $\nabla f$. When $f$ is given by equation (15), an upper bound for the Lipschitz constant for of is $$L = \frac{1}{\gamma}\left(\|A_0\|^2 + \sum_{i=0}^{N}\|A_i\|^2 + \|D\|^2\right).$$

This upper bound on the Lipschitz constant might be overly pessimistic, however, a line search procedure may be used when solving problem (14) by the proximal gradient method or by FISTA.

Below, one example of how to use the Chambolle-Pock algorithm to solve the general fluence map optimization problem (1) is described and depicted, under the assumption that the convex penalty functions $\Gamma$, $\Phi_i$, $\Psi$, and $\Theta$ have proximal operators that can be evaluated efficiently. This may include one or more (e.g., all) of penalty functions described previously.

Algorithm Derivation

Problem (1) can be expressed in the canonical form (9) by taking $f=\Theta$ and $$A = \begin{bmatrix} A_0 \\ A_0 \\ A_1 \\ \vdots \\ A_N \\ D \end{bmatrix},$$

$$g(v, y_0, y_1, \ldots, y_{N+1}) = \Gamma(v) + \sum_{i=0}^{N} \Phi_i(y_i) + \Psi(y_{N+1}).$$

(Note that $A_0$ appears twice in A.) Having expressed the fluence map optimization problem in the form (9), which is suitable for the Chambolle-Pock algorithm, it remains only to show how to compute the prox-operators of $f$ and $g^*$.

The prox-operator of $f$ is just the prox-operator of $\Theta$, and in some variations, may be evaluated efficiently. To see how to evaluate the prox-operator of $g^*$, first note that g is a separable sum. By the separable sum rule for conjugates $$g^*(w, z_0, \ldots, z_{N+1}) = \Gamma^*(w) + \sum_{i=0}^{N} \Phi_i^*(z_i) + \Psi^*(z_{N+1}).$$

Let t>0. The separable sum rule for prox-operators $$prox_{tg^*}(w, z_0, \ldots, z_{N+1}) = \begin{bmatrix} prox_{t\Gamma^*}(w) \\ prox_{t\Phi_0^*}(z_0) \\ \vdots \\ prox_{t\Phi_N^*}(z_N) \\ prox_{t\Psi^*}(z_{N+1}) \end{bmatrix}.$$

The Moreau decomposition theorem expresses the prox-operators of the functions $\Gamma^*$, $\Phi^*_i$, and $\Psi^*$ in terms of the prox-operators of the functions $\Gamma$, $\Phi_i$, and $\Psi$. These prox-operators are assumed to be inexpensive. Thus, it may be that the prox-operator of $g^*$ may be evaluated efficiently.

Table 1 depicted in FIG. 2 gives formulas for the prox-operators of the most typical penalty functions $\Gamma$, $\Phi_i$, $\Psi$, and $\Theta$. These formulas follow from the results listed in section 3, including the scaling and shifting rule (3.2).

Numerical Results

The Chambolle-Pock algorithm may be used to solve the fluence map optimization problem $$\underset{x}{\text{minimize}}\, \mu\|(A_0 x - \ell)_-\|_1 + \quad (10)$$

$$\sum_{i=0}^{N} \alpha_i\|(A_i x - u_i)_+\|_1 + \sum_{i=1}^{N} \frac{\beta_i}{2}\|A_i x\|_2^2 + \eta\|Dx\|_1$$

subject to $x \geq 0$.

Figure 10:
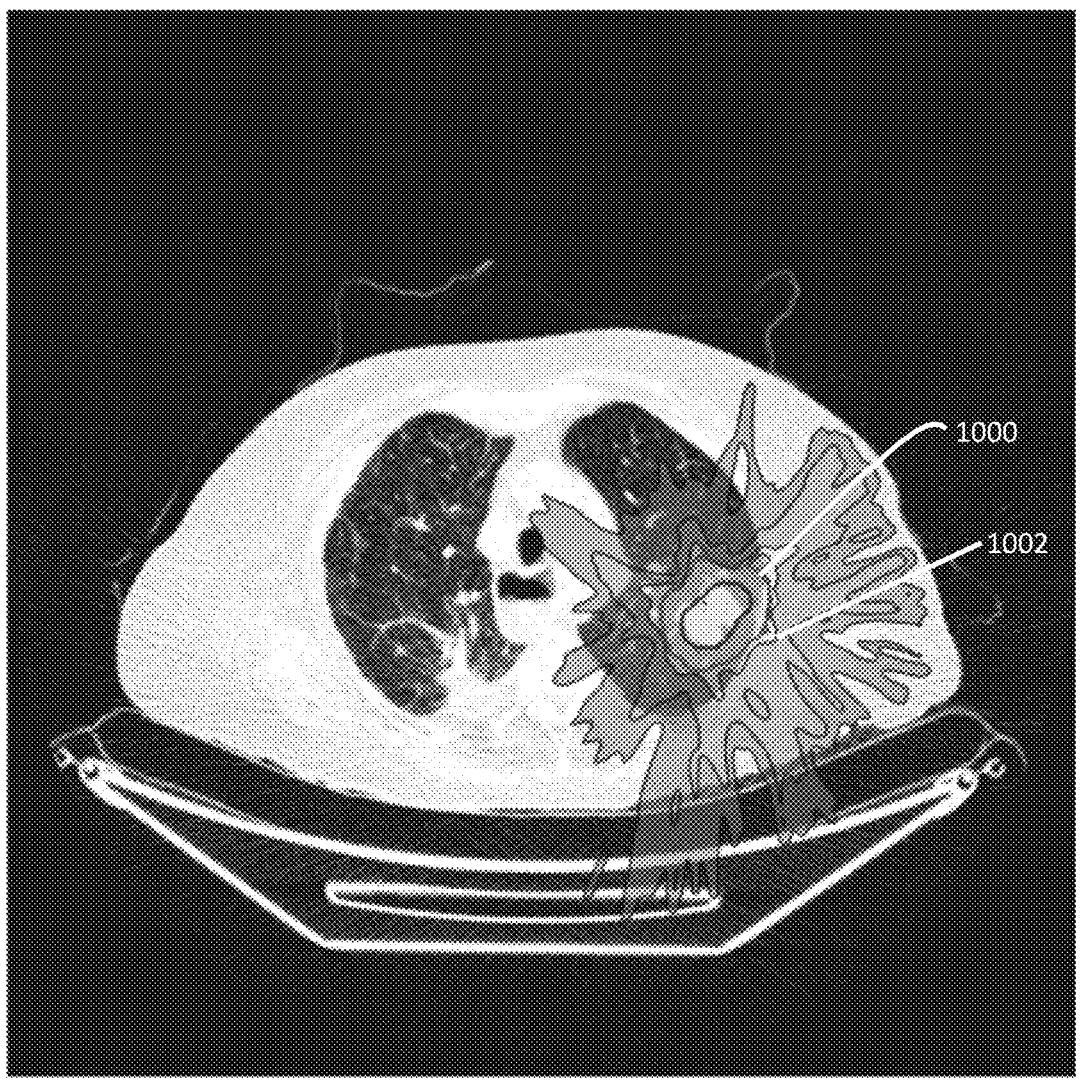
FIG. 10 depicts a dose distribution that results from a fluence map generation method comprising the Chambolle-Pock algorithm.
Figure 11:
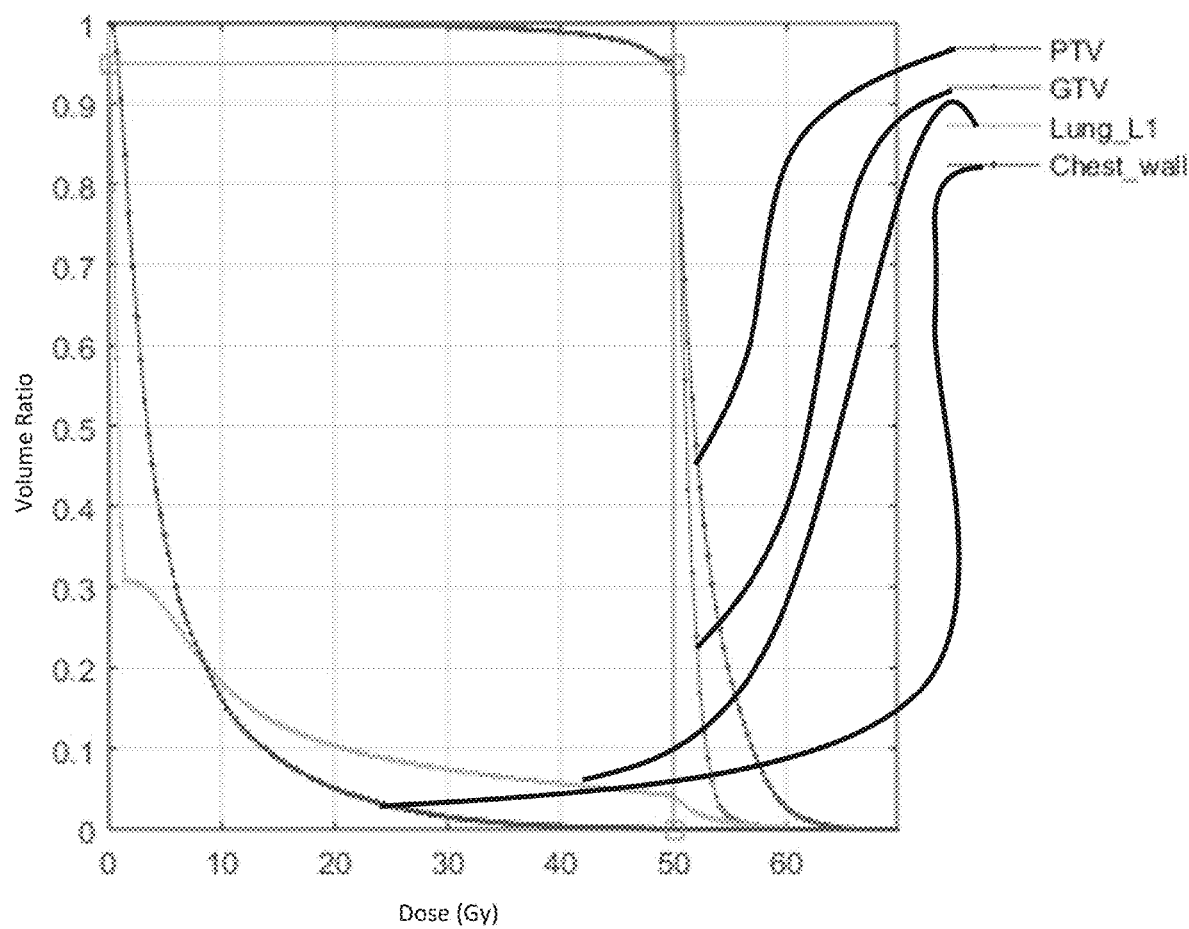
FIG. 11 is a dose-volume histogram of the dose distribution of FIG. 10.

Referring now to FIG. 10, the PTV is delineated by contour 1000. The region that receives at least 50 gray delineated by contour 1002 coincides almost exactly with the PTV contour 1000.

Stopping Criteria for FISTA

As explained above, the iterative portion of the fluence map generation method (e.g., accelerated proximal gradient methods such as FISTA or proximal algorithms such Chambolle-Pock) may exit once stopping criteria are attained (step 164 of the method 150). Fluence map generation or optimization methods comprising FISTA may have stopping criteria as described below.

A proximal gradient method (such as an accelerated proximal gradient method, including FISTA, as described herein) seeks to solve the primal problem:

$$\underset{x}{\text{minimize}}\, g(x) + h(x) \quad (11)$$

via the iteration $$x^+ = prox_{th}(x - t\nabla g(x)). \quad (12)$$

(Here h: $\mathbb{R}^N \to \mathbb{R} \cup \{\infty\}$ is a proper closed convex function, g: $\mathbb{R}^N \to \mathbb{R}$ is convex, differentiable, and has a Lipschitz continuous gradient, and t>0). The primal optimality condition for (11) is $$0 \in \nabla g(x) + \partial h(x). \quad (13)$$

A proximal gradient method may iterate to find r such that $$r \in \nabla g(x) + \partial h(x)$$

and r is nearly equal to 0, then this means that (13) is nearly satisfied and x is close to optimal.

$$x = \text{prox}_{th}(\hat{x}) \Leftrightarrow \frac{\hat{x} - x}{t} \in \partial h(x). \quad (14)$$

Using (14), equation (12) may be equivalent to $$\frac{x - t\nabla g(x) - x^+}{t} \in \partial h(x^+) \Leftrightarrow \frac{x - x^+}{t} \in \nabla g(x) + \partial h(x^+). \quad (15)$$

Condition (15) almost has the desired form, which may be rewritten equivalently as the following:

$$\frac{x - x^+}{t} + \nabla g(x^+) - \nabla g(x) \in \nabla g(x^+) + \partial h(x^+). \quad (16)$$

Condition (16) shows that $x^+$ is a nearly optimal, provided that the residual $$r = \frac{x - x^+}{t} + \nabla g(x^+) - \nabla g(x)$$

is small. Hence, a possible stopping criterion may be $\|r\| < \epsilon$. In some variations, a stopping criterion may include a "relative" residual, in which case the stopping criterion may be approximately:

$$\frac{\|r\|}{\|x^+\|} < \epsilon$$

FISTA solves (11) via the iteration $$y = x_{k-1} + \left(\frac{k-1}{k+2}\right)(x_{k-1} - x_{k-2}) \quad (17)$$

$$x_k = \text{prox}_{th}(y - t\nabla g(y)).$$

Equation (17) may be equivalent to:

$$\frac{y - t\nabla g(y) - x_k}{t} \in \partial h(x_k) \Leftrightarrow \frac{y - x_k}{t} + \nabla g(x_k) - \nabla g(y) \in \nabla g(x_k) + \partial h(x_k).$$

Hence the residual may be written as:

$$r = \frac{y - x_k}{t} + \nabla g(x_k) - \nabla g(y)$$

to get a stopping criterion for FISTA.

Alternatively, if a Lipschitz constant L for $\nabla g$ were known, a less computationally-intensive stopping criterion (i.e., which may not require evaluating the gradient of g at $x_k$) may include:

$$\|r\| \le \left\|\frac{y - x_k}{t}\right\| + \|\nabla g(x_k) - \nabla g(y)\| \le \frac{1}{t}\|y - x_k\| + L\|x_k - y\| =$$

$$\left(\frac{1}{t} + L\right)\|y - x_k\|$$

Stopping Criteria for Chambolle-Pock

Fluence map generation or optimization methods comprising Chambolle-Pock may have stopping criteria as described below. Chambolle-Pock solves the primal problem:

$$\underset{x}{\text{minimize}}\, F(Kx) + G(x) \quad (18)$$

and simultaneously the dual problem $$\underset{z}{\text{minimize}}\, G^*(-K^T z) + F^*(z)$$

via the iteration $$z^{n+1} = \text{prox}_{\sigma F^*}(z^n + \sigma K\bar{x}^n) \quad (19)$$

$$x^{n+1} = \text{prox}_{\tau G}(x^n - \tau K^T z^{n+1}) \quad (20)$$

$$\bar{x}^{n+1} = x^{n+1} + \theta(x^{n+1} - x^n). \quad (21)$$

In one variation, where a dual feasible variable may be available, a stopping criterion may be based on the duality gap. In the fluence map estimation problem, G is the indicator function for the nonnegative orthant, and it can be shown that G* is the indicator function for the nonpositive orthant. If the condition $-K^T z \le 0$ is met, z may be dual feasible. In some variations, this may not be satisfied by $z^{n+1}$. Moreover, in the fluence map estimation problem, $F^*(z)$ may be finite only when $z = (z_1, z_2, z_3)$ satisfies $\|z_2\|_\infty \le \lambda$ and $\|z_3\|_\infty \le \lambda$. These are additional constraints that z must satisfy to be dual feasible.

Alternatively, a stopping criterion may be based on residuals in KKT conditions. The Karush-Kuhn-Tucker (KKT) conditions are the set of necessary conditions for a solution of an optimization problem to be optimal, which can be expressed as a system of equations and inequalities involving the cost function and constraints on inputs. This may be used in certain variations where a stopping criterion based on the duality gap may be computationally intensive and/or where the conditions for a stopping criterion based on the duality gap are not met. The KKT conditions for the problem (18) can be written as $$0 \in K^T z + \partial G(x) \quad (22)$$

$$0 \in -Kx + \partial F^*(z). \quad (23)$$

The key idea for this stopping criterion is to find $r_1$ and $r_2$ such that $$r_1 \in K^T z + \partial G(x),$$

$$r_2 \in -Kx + \partial F^*(z)$$

and $r_1$ and $r_2$ are nearly equal to 0. If these conditions are met, then this means that (22) and (23) are nearly satisfied and x and z may be close to optimal.

Notably, x may be written as:

$$x = prox_{tf}(\hat{x}) \Leftrightarrow \frac{\hat{x} - x}{t} \in \partial f(x). \quad (24)$$

Using (24), equation (19) may be rewritten as follows:

$$\frac{z^n + \sigma K \bar{x}^n - z^{n+1}}{\sigma} \in \partial F^*(z^{n+1}) \Leftrightarrow \frac{z^n - z^{n+1}}{\sigma} \in -K\bar{x}^n + \partial F^*(z^{n+1}). \quad (25)$$

and (20) is equivalent to $$\frac{x^n + \tau K^T z^{n+1} - x^{n+1}}{\tau} \in \partial G(x^{n+1}) \Leftrightarrow \frac{x^n - x^{n+1}}{\tau} \in K^T z^{n+1} + \partial G(x^{n+1}). \quad (26)$$

As such, equation (25) may be expressed equivalently as:

$$\frac{z^n - z^{n+1}}{\sigma} + K(\bar{x}^n - x^{n+1}) \in -Kx^{n+1} + \partial F^*(z^{n+1}). \quad (27)$$

Conditions (26) and (27) taken together now show that $(x^{n+1}, z^{n+1})$ is a nearly optimal pair of primal and dual variables, provided that the residuals $$r_1 = \frac{x^n - x^{n+1}}{\tau} \text{ and } r_1 = \frac{z^n - z^{n+1}}{\sigma} + K(\bar{x}^n - x^{n+1})$$

are small. As such, one variation of a possible stopping criterion for Chambolle-Pock may be $\|r_1\| \le \epsilon$ and $\|r\| \le \epsilon$. In some variations, a stopping criterion may include a "relative" residual, in which case the stopping criterion may be approximately:

$$\frac{\|r_1\|}{\|x^{n+1}\|} < \epsilon, \frac{\|r_2\|}{\|z^{n+1}\|} < \epsilon$$

This stopping criterion may include an extra multiplication by K each iteration (e.g., $K(x^n - x^{n+1})$). To help reduce the computational load of additional multiplication by K and $K^T$, one variation of a method for generating a fluence map comprising a Chambolle-Pock method may be to check the stopping criteria or residuals at some iterations but not others. For example, the residuals may be calculated once every 20 or so iterations instead of every iteration. In other variations, the residuals may be calculated once every 2 iterations, once every 5 iterations, once every 10 iterations, once every 12 iterations, once every 25 iterations, once every 30 iterations, once every 50 iterations, etc. Alternatively, the residuals may be calculated at every iteration.

The FMO or fluence map generation methods described herein may be implemented by a computer or controller, for example, in a computer program or software stored in a machine-readable storage medium. The computer or controller may be part of a radiation therapy system such that a fluence map generated by the FMO or fluence map generation methods described herein may be used, for example, to position a radiation source at a particular angle with respect to the ROI or patient (by rotating a gantry on which the radiation source is mounted) and to adjust the beam intensity generated by the radiation source in accordance with the fluence map. Alternatively or additionally, the FMO or fluence map generation methods described herein may be implemented by a computer or controller that is separate from a radiation therapy system. The resultant fluence map may then be transferred to the controller of a radiation therapy system using a machine-readable transmission medium, such as (but not limited to) electrical, optical, acoustical, or other type of medium suitable for transmitting electronic information.

Controller

A system (e.g., a treatment planning system) that may be configured to generate fluence maps based on treatment plan parameters may comprise a controller in communication with a radiation therapy system and/or a clinician and/or operator. The controller may comprise one or more processors and one or more machine-readable memories in communication with the one or more processors. The controller may be connected to a radiation therapy system and/or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as the calculation of fluence maps based on treatment plan and/or clinical goals, segmentation of fluence maps into radiation therapy system instructions (e.g., that may direct the operation of the gantry, therapeutic radiation source, multi-leaf collimator, and/or any other components of a radiation therapy system and/or diagnostic or treatment planning system), and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the treatment planning system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to one or more support arms, external magnets, intracavity devices, and delivery devices.

Some variations of a treatment planning system for generating fluence maps may comprise a display device that may allow an operator to view graphical and/or textual representations of fluence maps, and/or dose distributions, and/or regions of interest, and/or volumes of interest, and/or patient anatomical images, and/or patient data (e.g., physiological and/or biological), and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system may be in communication with other computing devices (not shown) via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

The invention claimed is:

1. A method for calculating a fluence map for radiation therapy, the method comprising:
   selecting a volume of interest;
   selecting a plurality of voxels within the volume of interest, wherein each of the voxels has an acceptable dose range;
   selecting a set of candidate beamlets b={$b_i$} having initial beamlet intensity weights $x^0$={$x_i^0$};
   calculating a dose matrix A for the volume of interest based on the set of candidate beamlets b, wherein the dose matrix A contains per-voxel dose values delivered to each of the plurality of voxels by each of the candidate beamlets b; and
   calculating a fluence map having a final set of beamlet intensity weights $x^k$ by adjusting the initial beamlet intensity weights according to a proximal gradient method ($x^{k-1} \to x^k$) with a penalty function containing one or more linear penalties that iterates on the initial beamlet intensity weights until the adjusted beamlet intensity weights converge on a final set of beamlet intensity weights such that changes between iterations of the beamlet intensity weights are less than a predetermined residual criterion.

2. The method of claim 1, wherein the proximal gradient method is an accelerated proximal gradient method.

3. The method of claim 2, wherein the proximal gradient method is a fast iterative shrinkage-thresholding algorithm (FISTA).

4. The method of claim 1, wherein the one or more linear penalties comprises one or more $L_1$ penalties.

5. The method of claim 1, wherein the penalty function has been smoothed such that the penalty function is differentiable.

6. The method of claim 5, wherein the penalty function has been smoothed using Moreau-Yosida regularization.

7. The method of claim 1, wherein the initial set of beamlet intensity weights $\{x^0\}$ is an all-zero vector.

8. The method of claim 1, wherein the beamlets in the set of candidate beamlets b are divided between a smaller set of firing angles $\{f_i\}$.

9. The method of claim 8, wherein the set of firing angles $\{f_i\}$ comprises a plurality of angles around a patient area of a radiation treatment device.

10. The method of claim 9, wherein the plurality of firing angles are evenly distributed 360 degrees around the patient area.

11. The method of claim 1, wherein the proximal gradient method penalty function comprises one or more quadratic penalties.

12. The method of claim 11, wherein the one or more quadratic penalties comprises one or more $L_2$ penalties.

13. The method of claim 1, wherein the penalty function penalizes voxel dose excursions outside of the acceptable dose range.

14. The method of claim 13, wherein the penalty function is a single-value penalty function that aggregates the voxel dose excursions outside of the acceptable dose range of all of the voxels in the volume of interest.

15. The method of claim 1, wherein the acceptable dose range of each of the plurality of voxels is determined at least in part by a treatment plan.

16. The method of claim 1, wherein the volume of interest is a first volume of interest and the method further comprises:
    selecting a second volume of interest;
    selecting a second plurality of voxels within the second volume of interest, wherein each of the voxels has an acceptable dose range; and
    wherein calculating the dose matrix A further comprises calculating the dose matrix A for the first and second volumes of interest based on the set of candidate beamlets b, wherein the dose matrix A contains per-voxel dose values delivered to each of the first and second plurality of voxels by each of the candidate beamlets b.

17. The method of claim 1, further comprising segmenting the fluence map into a set of multi-leaf collimator and radiation source positioning instructions.

18. The method of claim 1, wherein the proximal gradient method penalty function comprises one or more indicator functions, the one or more indicator functions comprising an indicator function for an L∞-norm ball.

19. A system for calculating a fluence map for radiation therapy, the system comprising:
    a processor configured to:
      select a volume of interest;
      select a plurality of voxels within the volume of interest, wherein each of the voxels has an acceptable dose range;
      select a set of candidate beamlets b=$\{b_i\}$ having initial beamlet intensity weights $x^0=\{x_i^0\}$;
      calculate a dose matrix A for the volume of interest based on the set of candidate beamlets b, wherein the dose matrix A contains per voxel dose values delivered to each of the plurality of voxels by each of the candidate beamlets b;
      calculate a fluence map comprising a final set of beamlet intensity weights $x^k$ by adjusting the initial beamlet intensity weights according to a proximal gradient method update ($x^{k-1} \rightarrow x^k$) with a penalty function containing one or more linear penalties that iterates on the initial beamlet intensity weights until the adjusted beamlet intensity weights converge on a final set of beamlet intensity weights such that changes between iterations of the beamlet intensity weights are less than a predetermined residual criterion; and
      store the fluence map in a processor memory.

20. The system of claim 19, wherein the proximal gradient method is an accelerated proximal gradient method.

21. The system of claim 20, wherein the accelerated proximal gradient method is a fast iterative shrinkage-thresholding algorithm (FISTA).

22. The system of claim 19, wherein the one or more linear penalties comprises one or more $L_1$ penalties.

23. The system of claim 19, wherein the penalty function has been smoothed such that the penalty function is differentiable.

24. The system of claim 23, wherein the penalty function has been smoothed using Moreau-Yosida regularization.

25. The system of claim 19, wherein the penalty function penalizes voxel dose excursions outside of the acceptable dose range.

26. The system of claim 25, wherein the penalty function is a single-value penalty function that aggregates the voxel dose excursions outside of the acceptable dose range of all of the voxels in the volume of interest.

27. The system of claim 19, wherein the acceptable dose range of each of the plurality of voxels is determined at least in part by a treatment plan.

28. The system of claim 19, wherein the processor is further configured to:
    select a second volume of interest;
    select a second plurality of voxels within the second volume of interest, wherein each of the voxels has an acceptable dose range; and
    wherein calculating the dose matrix A further comprises calculating the dose matrix A for the first and second volumes of interest based on the set of candidate beamlets b, wherein the dose matrix A contains per-voxel dose values delivered to each of the first and second plurality of voxels by each of the candidate beamlets b.

29. The system of claim 19, further comprising a radiation therapy system comprising a therapeutic radiation source movable about a patient area and configured to apply radiation beamlets to the patient area according to the fluence map.

30. The system of claim 29, wherein a set of firing angles$\{f_i\}$ comprises a plurality of angles around the patient area of a radiation treatment device.

31. The system of claim 30, wherein the plurality of firing angles are evenly distributed 360 degrees around the patient area.

32. The system of claim 29, wherein the radiation therapy system further comprises a multi-leaf collimator disposed in a beam path of the therapeutic radiation source, and wherein the processor is configured to segment the fluence map into a set of multi-leaf collimator instructions and to transmit the instructions to the radiation therapy system.

33. The system of claim 29, wherein the radiation therapy system further comprises one or more PET detectors.

34. The system of claim 29, wherein the therapeutic radiation source is movable about the patient area at a speed of at least about 40 RPM.

35. The system of claim 19, wherein the proximal gradient method penalty function comprises one or more indicator functions, the one or more indicator functions comprising an indicator function for an L∞-norm ball.

\* \* \* \* \*